US011298422B2

(12) United States Patent
Krex et al.

(10) Patent No.: US 11,298,422 B2
(45) Date of Patent: Apr. 12, 2022

(54) TREATING TUMORS WITH TTFIELDS AND AN AURORA KINASE INHIBITOR

(71) Applicant: Novocure Limited, St. Helier (JE)

(72) Inventors: Dietmar Krex, Dresden (DE); Achim Temme, Dresden (DE); Rosa S. Shnaiderman, Haifa (IL); Moshe Giladi, Moshav Herut (IL)

(73) Assignee: Novocure GmbH, Root (CH)

( * ) Notice: Subject to any disclaimer, the term of this patent is extended or adjusted under 35 U.S.C. 154(b) by 438 days.

(21) Appl. No.: 16/377,599

(22) Filed: Apr. 8, 2019

(65) Prior Publication Data

US 2019/0307781 A1  Oct. 10, 2019

Related U.S. Application Data

(60) Provisional application No. 62/654,679, filed on Apr. 9, 2018, provisional application No. 62/826,114, filed on Mar. 29, 2019.

(51) Int. Cl.
| | | |
|---|---|---|
| *A61K 45/00* | (2006.01) | |
| *A61K 31/00* | (2006.01) | |
| *A61N 1/00* | (2006.01) | |
| *A61K 45/06* | (2006.01) | |
| *A61K 31/675* | (2006.01) | |
| *A61N 1/32* | (2006.01) | |
| *A61N 1/36* | (2006.01) | |
| *A61N 1/40* | (2006.01) | |
| *A61P 35/00* | (2006.01) | |
| *A61K 31/55* | (2006.01) | |
| *A61K 33/42* | (2006.01) | |

(52) U.S. Cl.
CPC .............. *A61K 45/06* (2013.01); *A61K 31/55* (2013.01); *A61K 31/675* (2013.01); *A61K 33/42* (2013.01); *A61N 1/32* (2013.01); *A61N 1/36002* (2017.08); *A61N 1/40* (2013.01); *A61P 35/00* (2018.01)

(58) Field of Classification Search
CPC ........ A61K 45/06; A61K 31/675; A61N 1/32; A61N 1/40; A61P 35/00
See application file for complete search history.

(56) References Cited

U.S. PATENT DOCUMENTS

| | | | |
|---|---|---|---|
| 6,868,289 B2 | 3/2005 | Palti | |
| 7,016,725 B2 | 3/2006 | Palti | |
| 7,089,054 B2 | 8/2006 | Palti | |
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 9,910,453 B2 | 3/2018 | Wasserman et al. | |

(Continued)

FOREIGN PATENT DOCUMENTS

WO    2005002571 A1    1/2005

OTHER PUBLICATIONS

Bavetsias et al., "Aurora Kinase Inhibitors: Current Status and Outlook," Frontiers in Oncology, vol. 5, Article 278, Dec. 2015.
Giladi et al., "Tumor Treating Fields (TTFields) Delay DNA Damage Repair Following Radiation Treatment of Glioma Cells: Implications for Irradiation Through TTFields Transducer Arrays," International Journal of Radiation Oncology, vol. 99, No. 2, p. S32, Sep. 2017.
Hong et al., "The selective Aurora-A kinase inhibitor MLN8237 (alisertib) potently inhibits proliferation of glioblastoma neurosphere tumor stem-like cells and potentiates the effects of temozolomide and ionizing radiation," Cancer Chemother. Pharmacol., vol. 73, pp. 983-990, Mar. 2014.

(Continued)

*Primary Examiner* — Sikarl A Witherspoon
(74) *Attorney, Agent, or Firm* — Potomac Law Group, PLLC

(57) ABSTRACT

The viability of cancer cells can be reduced by administering an Aurora kinase inhibitor (e.g., MLN8237 or another Aurora A kinase inhibitor, AZD1152 or another Aurora B kinase inhibitor) to the cancer cells, and applying an alternating electric field with a frequency between 100 and 300 kHz (e.g., 200 kHz) to the cancer cells. Furthermore, cancer (e.g., glioblastoma) in a subject may be treated by administering an Aurora kinase inhibitor to the subject, and applying an alternating electric field with frequency between 100 and 300 kHz (e.g., 200 kHz) to a target region of the subject (e.g., the brain).

27 Claims, 21 Drawing Sheets

(56) References Cited

U.S. PATENT DOCUMENTS

| 10,188,851 B2 | 1/2019 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |

OTHER PUBLICATIONS

International Search Report and Written Opinion for International Application No. PCT/IB2019/052885 dated Jul. 19, 2019.
Wiedemuth et al., "Janus face-like effects of Aurora B inhibition: antitumoral mode of action versus induction of aneuploid progeny," Carcinogenesis, vol. 37, No. 10, pp. 993-1003, Aug. 2016.
Giladi et al., "Mitotic Spindle Disruptions by Alternating Electric Fields Leads to Improper Chromosome Segregation and Mitotic Catastrophe in Cancer Cells," Scientific Reports, vol. 5, No. 1, pp. 1-16, Dec. 2015.

U87-MG | 0 nM AZD1152

U87-MG | 50 nM AZD1152

U87-MG | 100 nM AZD1152

U87-MG Shp53 | 0 nM AZD1152

U87-MG Shp53 | 12.5 nM AZD1152

U87-MG Shp53 | 25 nM AZD1152

U87-MG Shp53 | 100 nM AZD1152

TREATING TUMORS WITH TTFIELDS AND AN AURORA KINASE INHIBITOR

CROSS REFERENCE TO RELATED APPLICATIONS

This Application claims the benefit of U.S. Provisional Application 62/654,679 filed Apr. 9, 2018, and U.S. Provisional Application 62/826,114 filed Mar. 29, 2019, each of which is incorporated herein by reference in its entirety.

BACKGROUND

Tumor Treating Fields (TTFields) are an effective antineoplastic treatment modality delivered via application of low intensity, intermediate frequency, alternating electric fields. To date, TTFields therapy has received FDA approval for treating Glioblastoma Multiforme brain tumors. In one example, TTFields therapy is delivered using a wearable and portable device (Optune®). The delivery system can include four adhesive, non-invasive, insulated "transducer arrays", an electric field generator, rechargeable batteries, and a carrying case. The transducer arrays can be applied to the skin in the vicinity of the tumor and connected to the field generator.

In the preclinical setting, TTFields can be applied in vitro using, for example, the Inovitro™ TTFields lab bench system. Inovitro™ includes a TTFields generator and base plate containing 8 ceramic dishes per plate. Cells are plated on a 22 mm round cover slip placed inside each dish. TTFields are applied using two perpendicular pairs of transducer arrays insulated by a high dielectric constant ceramic in each dish. The orientation of the TTFields in each dish is switched 90° every 1 second, thus covering the majority of the orientation axis of cell divisions.

SUMMARY

Certain types of cancer (e.g., glioblastoma) may be ameliorated or treated with a TTFields and an Aurora kinase inhibitor (e.g., Barasertib (AZD1152), Alisertib (MLN8237), Danusertib (PHA-739358), AT9283, PF-03814735, and AMG 900). See, e.g., Bavetsias, et. al., Aurora Kinase Inhibitors: Current Status and Outlook, Front Oncol. 2015; 5: 278. All cited references and publications are incorporated herein in their entirety.

One aspect of the invention is directed to a first method of reducing viability of cancer cells. The first method comprises administering an Aurora kinase inhibitor to the cancer cells; and applying an alternating electric field to the cancer cells, the alternating electric field having a frequency between 100 and 300 kHz.

In some instances of the first method, the Aurora kinase inhibitor is an Aurora A kinase inhibitor. In some instances of the first method, the Aurora A kinase inhibitor comprises Alisertib (MLN8237).

In some instances of the first method, the Aurora kinase inhibitor is an Aurora B kinase inhibitor. In some instances of the first method, the Aurora B kinase inhibitor comprises AZD1152. In some instances of the first method, the Aurora B kinase inhibitor is selected from the group consisting of AZD1152, Alisertib (MLN8237), Danusertib (PHA-739358), AT9283, PF-03814735, and AMG 900.

In some instances of the first method, at least a portion of the applying step is performed simultaneously with at least a portion of the administering step. In some instances of the first method, the applying step has a duration of at least 72 hours. The application of the electrical field for 72 hours may be accomplished in a single 72 hour interval. Alternatively, the application of the electrical field could be interrupted by breaks. For example, 6 sessions with a duration of 12 hours each, with a 2 hour break between sessions.

In some instances of the first method, the frequency of the alternating electric field is between 180 and 220 kHz.

In some instances of the first method, the Aurora kinase inhibitor is administered to the cancer cells at a therapeutically effective concentration, and the alternating electric field has a field strength of at least 1 V/cm in at least some of the cancer cells.

In some instances of the first method, the Aurora kinase inhibitor is administered to the cancer cells at a therapeutically effective concentration that is reduced by at least 50% with respect to a dosage of the Aurora kinase inhibitor known to be therapeutically effective in the absence of an alternating electric field, and the alternating electric field has a field strength of at least 1 V/cm in at least some of the cancer cells.

In some instances of the first method, the Aurora kinase inhibitor is administered to the cancer cells at a therapeutically effective concentration from about 12.5 nM to about 100 nM, and the alternating electric field has a field strength of at least 1 V/cm in at least some of the cancer cells.

In some instances of the first method, the Aurora kinase inhibitor is administered to the cancer cells at a therapeutically effective concentration from 25 nM to 75 nM, and the alternating electric field has a field strength of at least 1 V/cm in at least some of the cancer cells.

Another aspect of the invention is directed to a second method of treating cancer in a subject. The second method comprises administering a therapeutically effective dose of an Aurora kinase inhibitor to the subject; and applying an alternating electric field to a target region of the subject, the alternating electric field having a frequency between 100 and 300 kHz.

In some instances of the second method, the Aurora kinase inhibitor comprises an Aurora A kinase inhibitor. In some instances of the second method, the Aurora kinase inhibitor comprises an Aurora B kinase inhibitor. In some instances of the second method, the Aurora kinase inhibitor comprises AZD1152. In some instances of the second method, the Aurora kinase inhibitor comprises MLN8237. In some of these instances of the second method, the cancer comprises Glioblastoma.

In some instances of the second method, the Aurora kinase inhibitor is selected from the group consisting of AZD1152, MLN8237, Danusertib (PHA-739358), AT9283, PF-03814735, and AMG 900.

In some instances of the second method, at least a portion of the applying step is performed after the administering step and before the Aurora kinase inhibitor is eliminated from the subject's body or exhausted.

In some instances of the second method, the applying step has a duration of at least 72 hours. The application of the electrical field for 72 hours may be accomplished in a single 72 hour interval. Alternatively, the application of the electrical field could be interrupted by breaks. For example, 6 sessions with a duration of 12 hours each, with a 2 hour break between sessions.

In some instances of the second method, the frequency of the alternating electric field is between 180 and 220 kHz.

In some instances of the second method, the alternating electric field has a field strength of at least 1 V/cm in at least a portion of the target region.

In some instances of the second method, the therapeutically effective dose of the Aurora kinase inhibitor is reduced by at least 50% with respect to a dosage of the Aurora kinase inhibitor known to be therapeutically effective in the absence of an alternating electric field. In some instances of the second method, the therapeutically effective dose of the Aurora kinase inhibitor is from about 12.5 nM to about 100 nM. In some instances of the second method, the therapeutically effective dose of the Aurora kinase inhibitor is from 25 nM to 75 nM.

DETAILED DESCRIPTION OF THE PREFERRED EMBODIMENTS

Figure 1A:
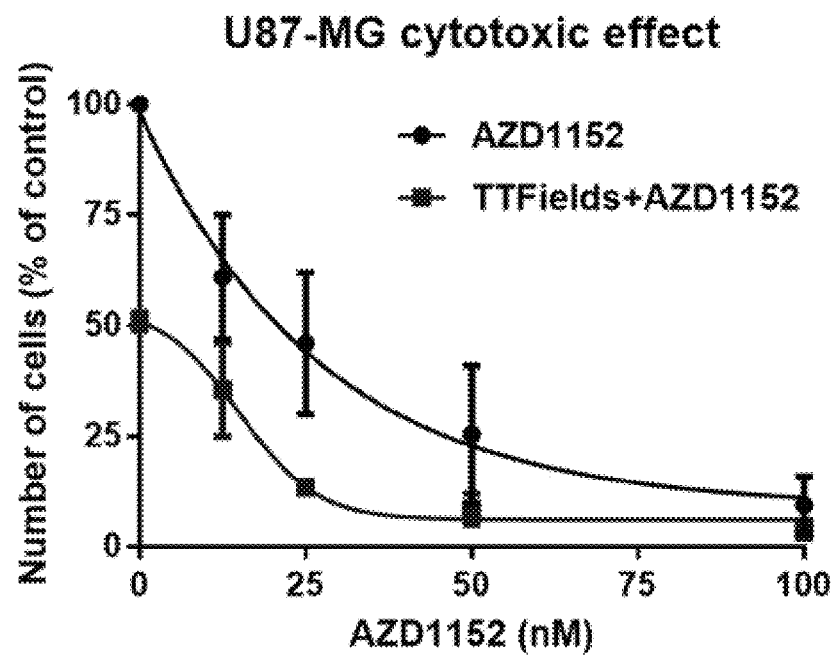
FIGS. 1A-1E show the exemplary effects of TTFields and AZD1152 on U87-MG, U87-MG$^{shp53}$, and U-251 glioma cells at various AZD1152 concentrations.

The term "treating" refers to ameliorating, inhibiting, reducing growth, inhibiting metastases, and prescribing medication to do the same. The Aurora B kinase inhibitors described herein can be used in combination with a pharmaceutically acceptable carrier for administration to a patient. The term "reducing viability," as used herein, refers to decreasing proliferation, inducing apoptosis, or killing cancer cells. The term "therapeutically effective concentration," as used herein, refers to a concentration of a drug or drugs sufficient to achieve its intended purpose (e.g., treatment of cancer). See, e.g., Schwartz et. al., *Phase I study of barasertib (AZD1152), a selective inhibitor of Aurora B kinase, in patients with advanced solid tumors*, Invest New Drugs. 2013 April; 31(2):370-80 (maximum tolerated AZD1152 dose of 150 mg as a 48-h continuous infusion and 220 mg administered as two 2-h infusions (110 mg/day, days 1, 2, 15 and 16)); Kantarjian et al., *Phase I study assessing the safety and tolerability of barasertib (AZD1152) with low-dose cytosine arabinoside in elderly patients with AML*, Clin Lymphoma Myeloma Leuk. 2013 October; 13(5):559-67.

Introduction

TTFields exert directional forces on polar microtubules and interfere with the assembly of the normal mitotic spindle. Such interference with microtubule dynamics results in abnormal spindle formation and subsequent mitotic arrest or delay. Cells can die while in mitotic arrest or progress to cell division. This can lead to the formation of either normal or abnormal aneuploid progeny. The formation of the tetraploid cells can occur either due to mitotic exit through slippage or can occur during improper cell division. Abnormal daughter cells can die in the subsequent interphase, can undergo a permanent arrest, or can proliferate through additional mitosis where they will be subjected to further TTFields assault. See M. GILADI et al. Mitotic Spindle Disruption by Alternating Electric Fields Leads to Improper Chromosome Segregation and Mitotic Catastrophe in Cancer Cells, Scientific Reports, 2015; 5:18046, which is incorporated herein by reference in its entirety.

A promising approach to enhance the efficiency of TTFields is the use of drugs which synergistically act together with TTFields and which extend metaphase-anaphase transition and telophase. Specifically, inhibitors or drugs interfering with components of the chromosomal passenger complex, in particular affecting Aurora B kinase, are excellent candidates for combinatorial use with TTFields.

Aurora B represents a chromosomal passenger protein (CPP). It assembles in a stable complex with the inner centromeric protein (INCENP/INCENP), BIRC5/Survivin, and CDCA8/Borealin to build the chromosomal passenger complex (CPC). Aurora B kinase activity is involved in correcting syntelic and merotelic microtubule-kinetochore connections and therefore is an important factor in bioorientation of sister chromatids to opposing spindle poles before onset of anaphase. Aurora B, in cooperation with its partners of the CPC, safeguards segregation, chromosomal integrity independently of p53 mutational status and therefore is important for survival of cells. See R WIEDEMUTH R et al. Janus Face-Like Effects of Aurora B Inhibition: Antitumoral Mode of Action Versus Induction of Aneuploid Progeny, Carcinogenesis, 2016; 37(10):993-1003, which is incorporated herein by reference in its entirety.

The studies described herein were run to test the hypothesis that TTFields effect on tumor cells can be exaggerated by an additional inhibition of cytokinesis through chemical inhibition of an Aurora kinase. More specifically, the studies explored combining TTFields and the Aurora B kinase inhibitor AZD1152 for the treatment of GBM. In another instance, additional Aurora B kinase inhibitors can be used before, during, or after treatment with TTFields including, but not limited to, Danusertib (PHA-739358), AT9283, PF-03814735, and AMG 900. Aurora A kinase is associated with centrosome maturation and separation and affects spindle assembly and stability. See, e.g., Cummings, et. al.,

*Biphasic activation of Aurora-A kinase during the meiosis I-meiosis II transition in Xenopus oocytes*, Mol. Cell. Biol. 23 (5): 1703-16.

The effects of the combined treatment of TTFields and the Aurora B kinase inhibitor AZD1152 was tested in 3 different glioma cell lines: U87-MG, U87-MG$^{shp53}$ and U-251. TTFields (1.75 V/cm RMS, 200 kHz) were applied for 72 hours using the Inovitro system. AZD1152 was added to the media in concentrations of up to 100 nmol/L. Cell counts, cell cycle, and clonogenic potential were determined at the end of treatment. Formation of multinuclear cells was determined using microscopic images of cells stained with crystal violet.

The combined treatment with TTFields and AZD1152 led to a significant reduction in the number of U251, U87-MG and U87-MG$^{shp53}$ cells (2-way ANOVA, $p<0.001$ in all three cell lines) as compared to each treatment alone. The overall effect, taking into account not just the cytotoxic effect at the end of treatment, but also the clonogenic potential, demonstrated a significant reduction in U87-MG, U87-MG$^{shp53}$ and U-251 cells (2-way ANOVA, $p<0.001$ in all 3 cell lines) as compared to each treatment alone. Microscopy images of U87-MG and U87-MG$^{shp53}$ cells stained with crystal violet after treatment, revealed high prevalence of multi nuclear cells in cells exposed to TTFields and AZD1152 (25 nM) as compared to cells treated with AZD1152 (25 nM) alone. Cells treated with TTFields and higher doses of AZD1152 (50-100 nM) demonstrated increased rates of pyknosis.

The results described herein demonstrate that the combination of TTFields and the Aurora B kinase inhibitor AZD1152 can be an effective treatment against glioma cells, and that synergy appears to be present between those two treatment modalities. The results described herein also demonstrate that the combination of TTFields and the Aurora A kinase inhibitor MLN8237 can be an effective treatment against glioma cells Methods Cell Culture and Drugs The effects of the combined treatment of TTFields and AZD1152 was tested using the following human glioma cell lines: U87-MG (ATCC), U-251 (ECACC) and U87-mG$^{shp53}$ (provided by Dr. Achim Temme). All cells were grown in a humidified incubator supplied with 5% CO2. Cells were maintained in EMEM, supplemented with 10% FBS, 2 mmol/L glutamine, Pen-Strep solution (100 units/ml Penicillin and 0.1 mg/ml Streptomycin), 1 mmol/L sodium pyruvate and 1% NEAA. U87-MG$^{shp53}$ cells were maintained under selection with 400 mg/mL geneticin. AZD1152 was obtained from Sigma, Israel.

Cytotoxicity Assay and Overall Effect

TTFields (1.6 V/cm RMS, 200 kHz) were applied for 72 hours using the Inovitro system. At the end of treatment, inhibition of tumor cell growth was analyzed quantitatively based on cell count. Clonogenic survival of U87-MG, U87-MG$^{shp}$53 and U-251 was tested by plating triplicates of 300 cells/dish in 6 wells dishes. After 2-3 weeks, cells were stained with crystal violet and the number of clones was quantified. Overall effect was calculated by multiplying the percentage of surviving cells at the end of treatment with the percentage of colonies formed vs. control.

Flow Cytometry

For cell cycle analysis, cells were removed with Trypsin immediately after 72 h treatment, washed twice with ice-cold PBS with 1% FBS and fixed with 70% ice-cold ethanol for 30 min. After fixation, cells were washed twice with ice-cold PBS with 1% FBS, pelleted and incubated in PBS containing 10 μg/ml RNase and 7.5 μg/ml7-AAD (Sigma-Aldrich) at 37° C. for 30 min. Cell cycle distribution was then quantified using the EC800 flow cytometer (Sony Biotechnology, Japan).

Microscopy

At the end of treatment, cells were fixed with 100% methanol, stained with 0.5% crystal violet (Sigma) and imaged under inverted microscope (Nikon eclipse TS100).

Statistical Analysis

Data is expressed as mean±SE, and the statistical significance of differences was assessed using GraphPad Prism 6 software (GraphPad Software, La Jolla, Calif.). Differences between groups were compared using 2-way ANOVA, and were considered significant at values of $0.05>*p>0.01$, $p<0.01$, and $*p<0.001$.

Results

Figure 1B:
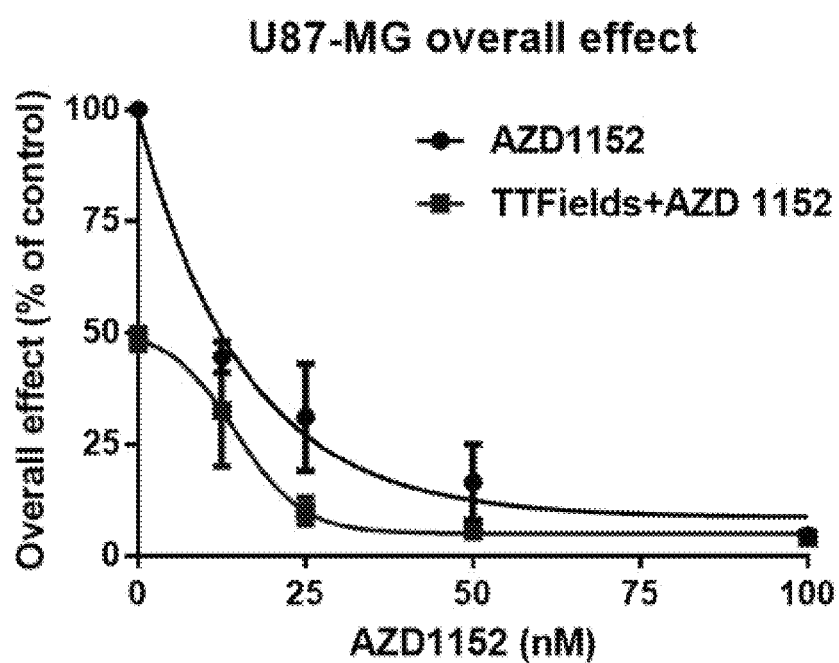

FIGS. 1A-E depict the effects of TTFields and AZD1152 on glioma cells. U87-MG, U87-MG$^{shp}$53 and U-251 glioma cells grown in various AZD1152 concentrations and treated with TTFields (200 kHz, 1.6 V/cm RMS) for 72 hours. U87-MG proved to be highly sensitive to treatment with AZD1152 at concentrations above 20 nM. As depicted in FIG. 1A, the response to TTFields application alone led to about 50% reduction in the number of cells. The number of cells was determined at the end of treatment and is expressed as percentage of control. The combined treatment of TTFields and AZD1152 led to a significant enhancement of the cytotoxic effect (2-way ANOVA, $p<0.001$). In addition, as depicted in FIG. 1B, the combined treatment of TTFields and AZD1152 led to a significant enhancement of the overall effect in U87-MG cells taking into consideration both the cytotoxic effect and the clonogenic response.

Figure 1C:
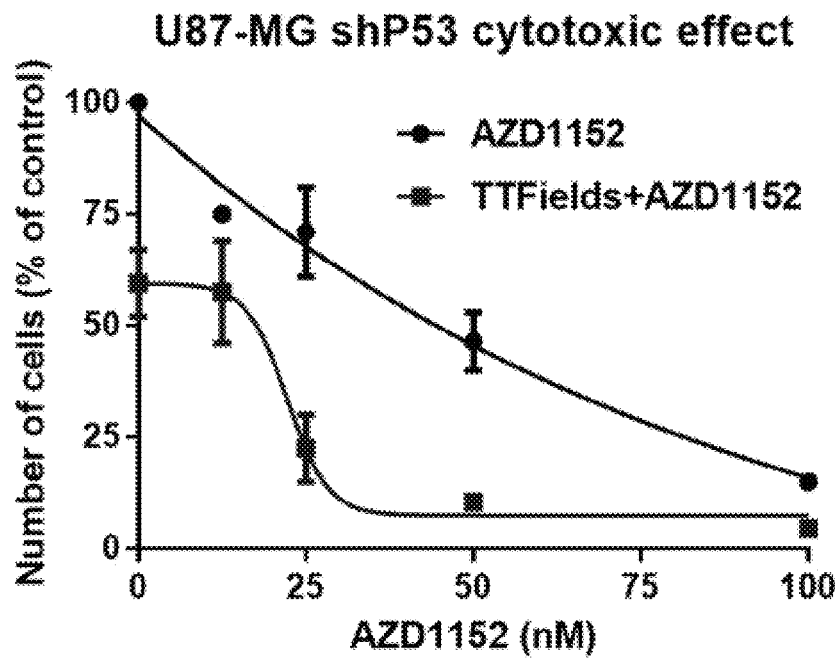

U87-MG$^{shp53}$ proved to be less sensitive to treatment with AZD1152 as compared to their p53 WT counterpart strain with an IC-50 of around 50 nM. Response to TTFields application alone led to about 40% reduction in the number of U87-MG$^{shp53}$ cells, which is only slightly less than the reduction observed for their p53 WT counterpart strain (FIG. 1C). The combined treatment of TTFields and AZD1152 led to a significant enhancement of the cytotoxic effect (2-way ANOVA, $p<0.001$) (FIG. 1D) and the overall effect (FIG. 1D) in U87-MG$^{shp53}$ cells.

Figure 1D:
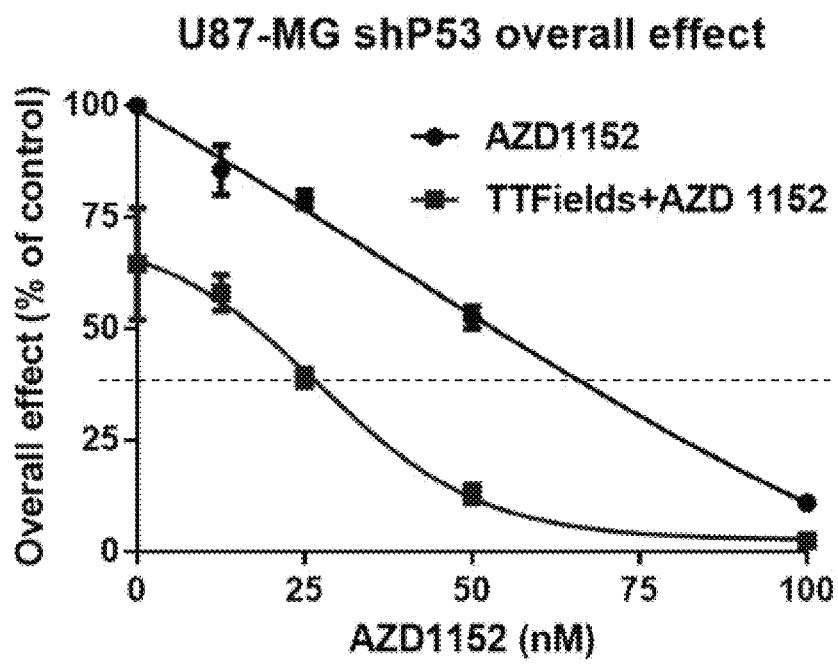

Notably, when AZD1152 is combined with TTFields, the dosage of AZD1152 required to obtain a given level of overall effect can often be reduced by at least 50% with respect to the dosage of AZD1152 that provides the same given level of overall effect in the absence of an alternating electric field. For example, the dashed horizontal line in FIG. 1D shows that a dosage of 70 nM of AZD1152 is required to achieve an overall effect of 38% in the absence of TTFields, and that a dosage of only 25 nM of AZD1152 is required to achieve the same overall effect of 38% when AZD1152 is combined with TTFields.

Figure 1E:
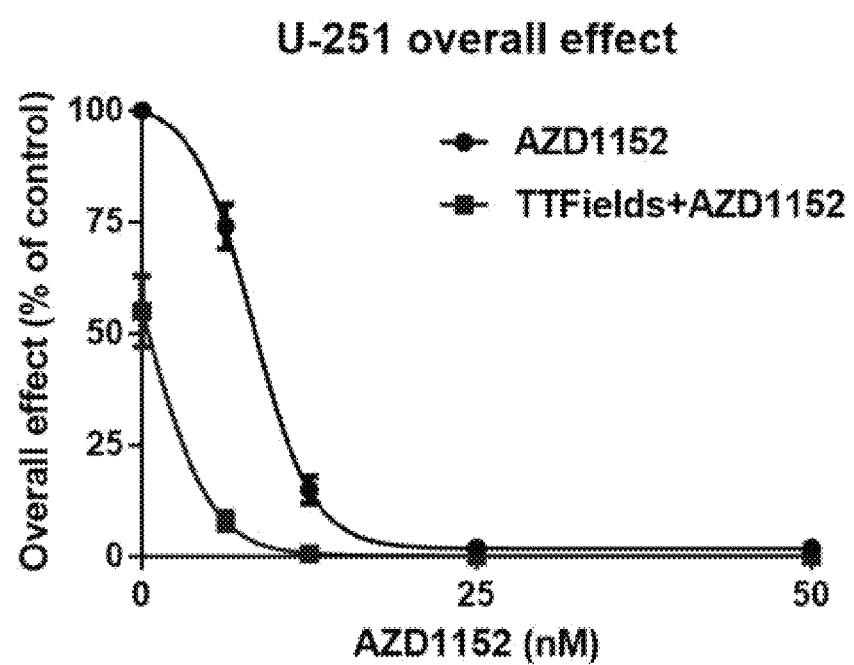

U-251 cells increased their volume dramatically following treatment with AZD1152, which made them impossible to count using flow cytometry. The overall effect for U-251 cells was determined based on the clonogenic assay. Response to TTFields application alone led to about 50% reduction in the clonogenic potential of U-251 cells (FIG. 1E). The combined treatment of TTFields and AZD1152 led to a significant reduction in the number of U-251 colonies (2-way ANOVA, $p<0.001$) (FIG. 1E).

Figure 2A:
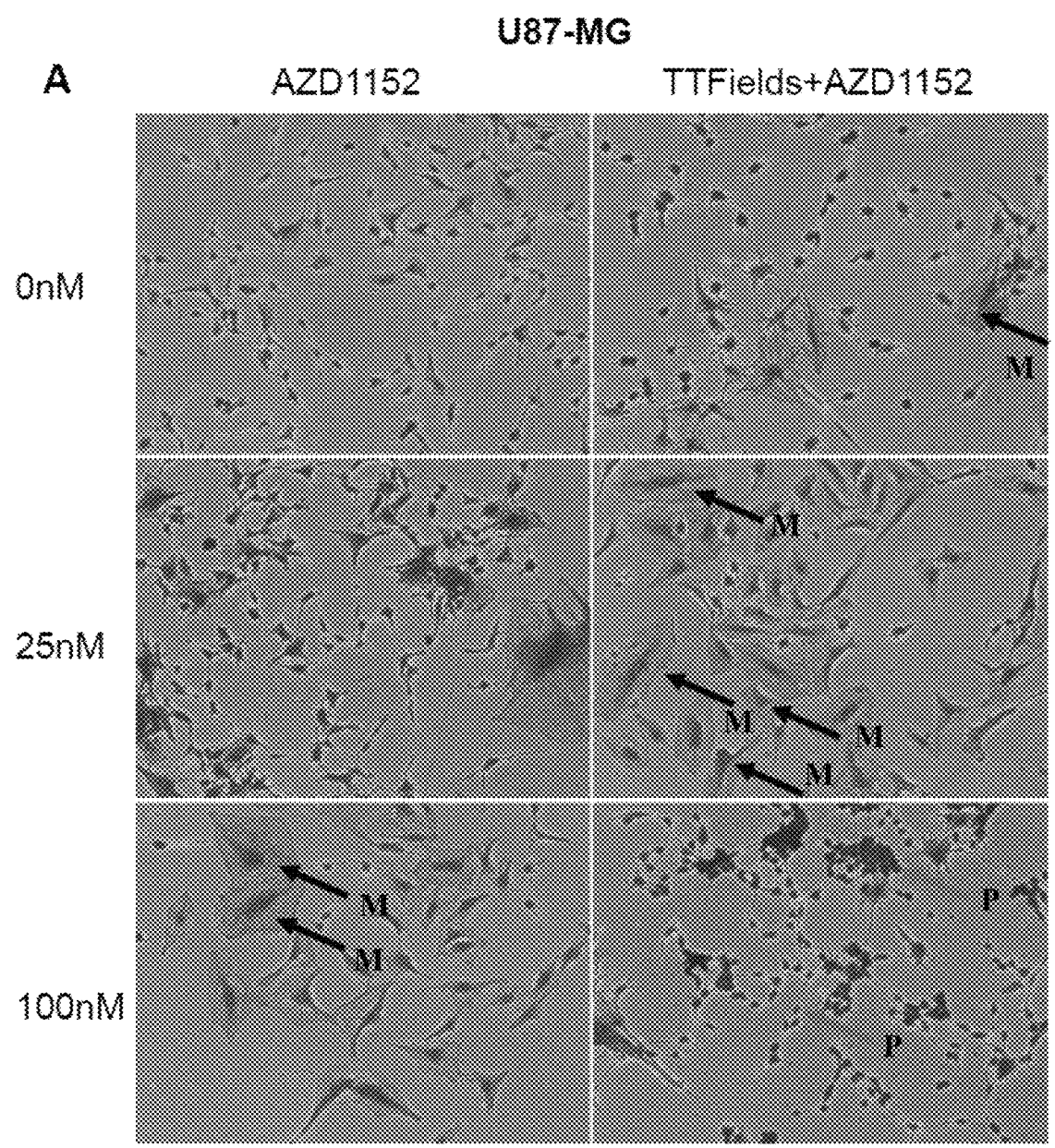
FIGS. 2A and 2B are exemplary microscopy images of U87-MG and U87-mG$^{shp53}$ cells, respectively, that show the formation of multinuclear and pyknotic cells following treatment with TTFields and AZD1152.
Figure 2B:
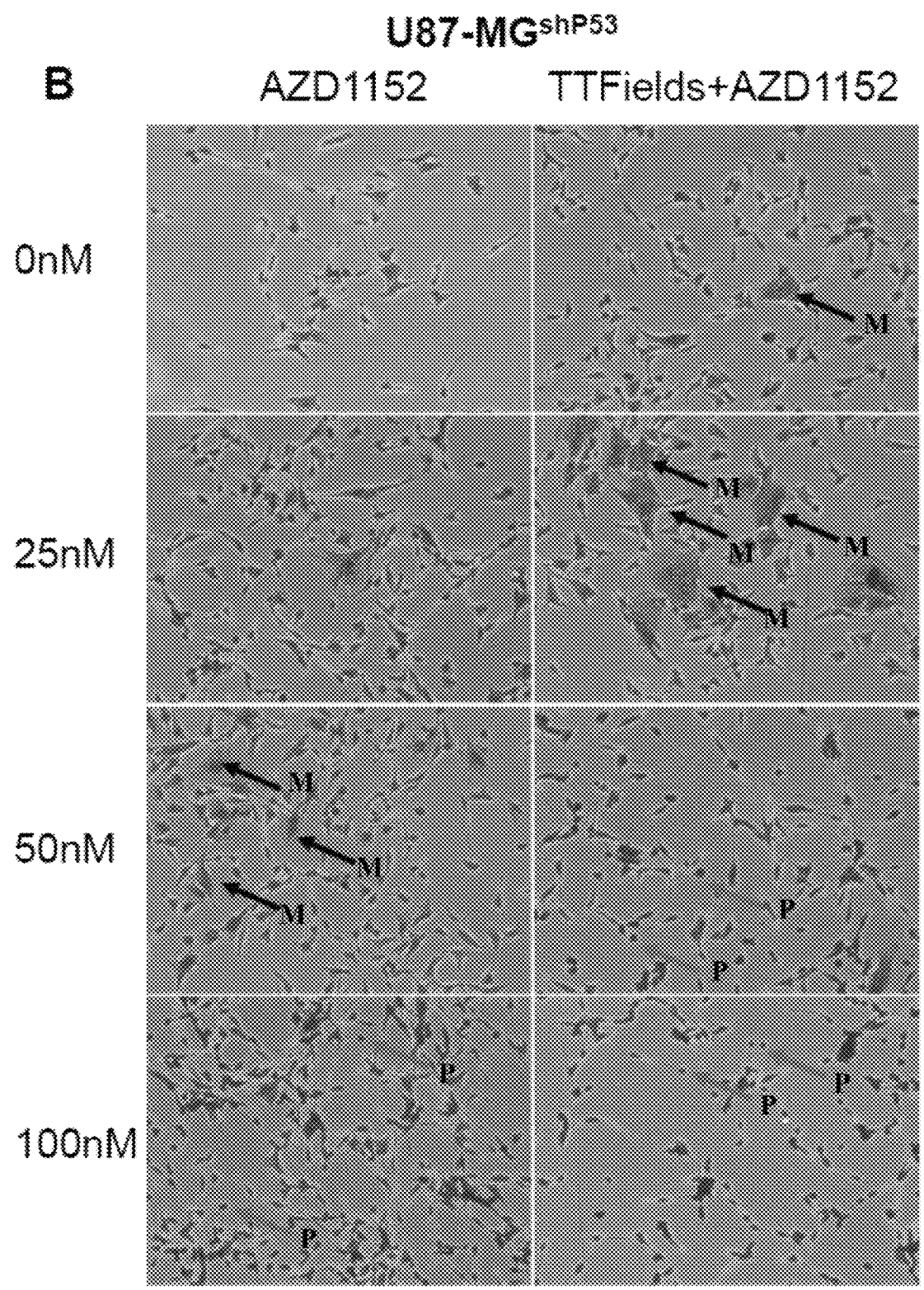
Figure 3A:
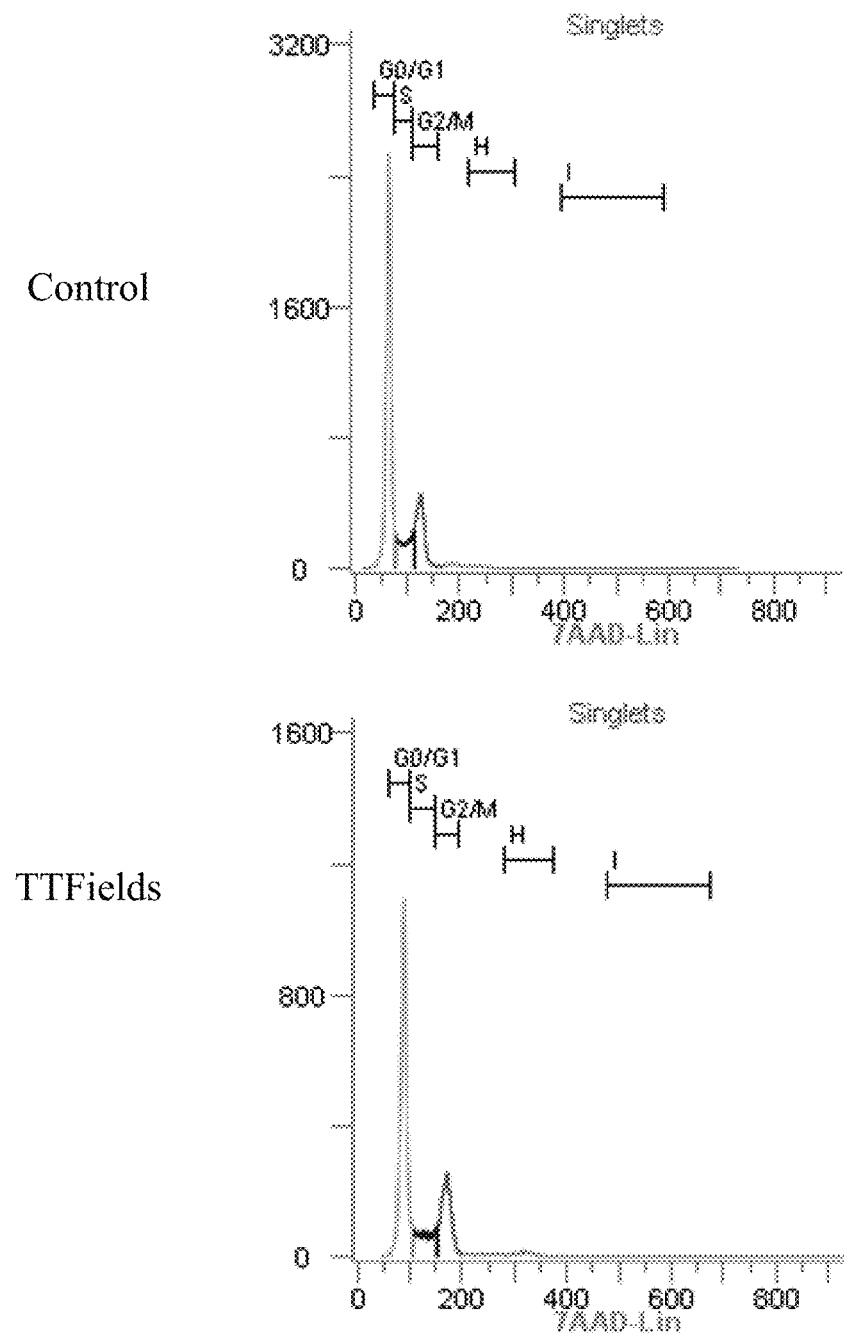
FIGS. 3A-3D show the exemplary increase in polyploidy in U87-MG cells following treatment with TTFields at various AZD1152 concentrations.
Figure 3B:
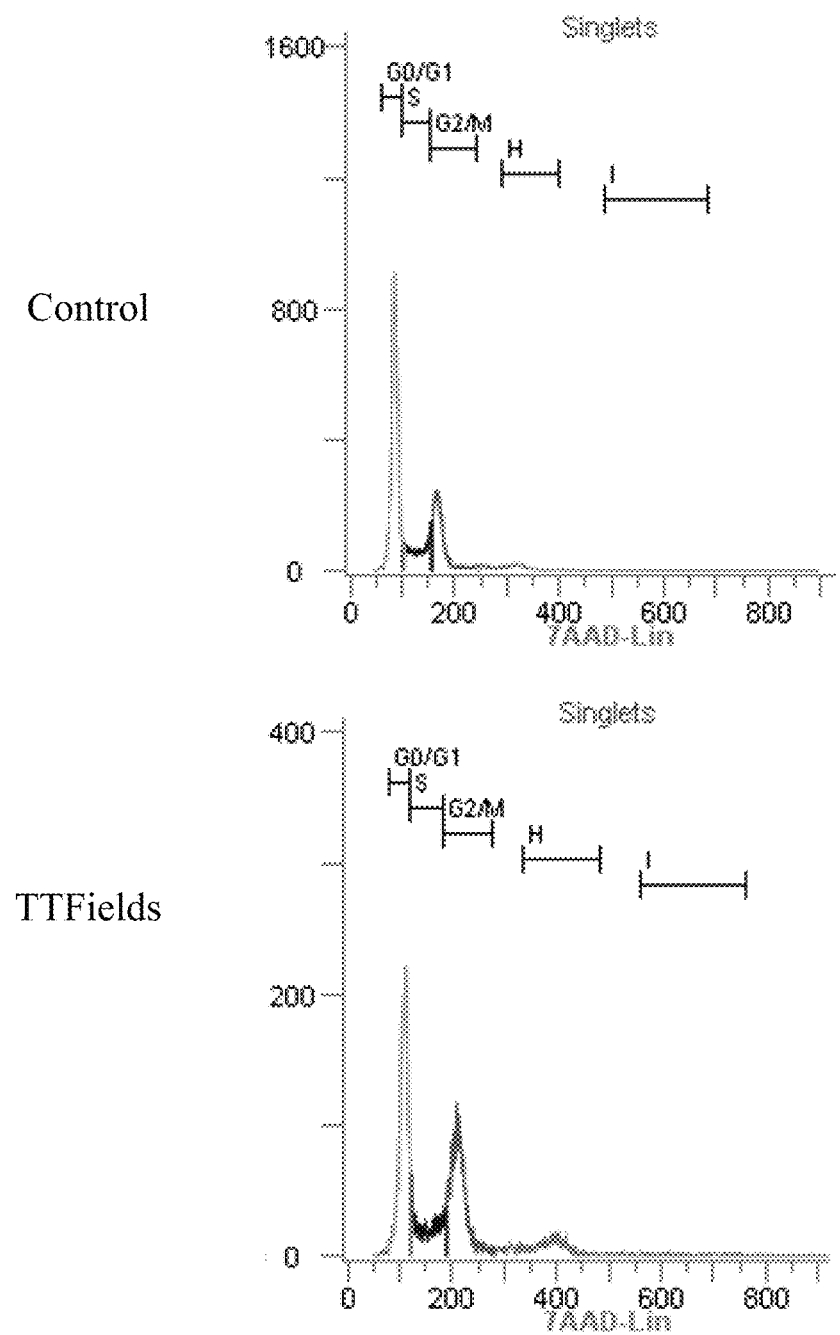
Figure 3C:
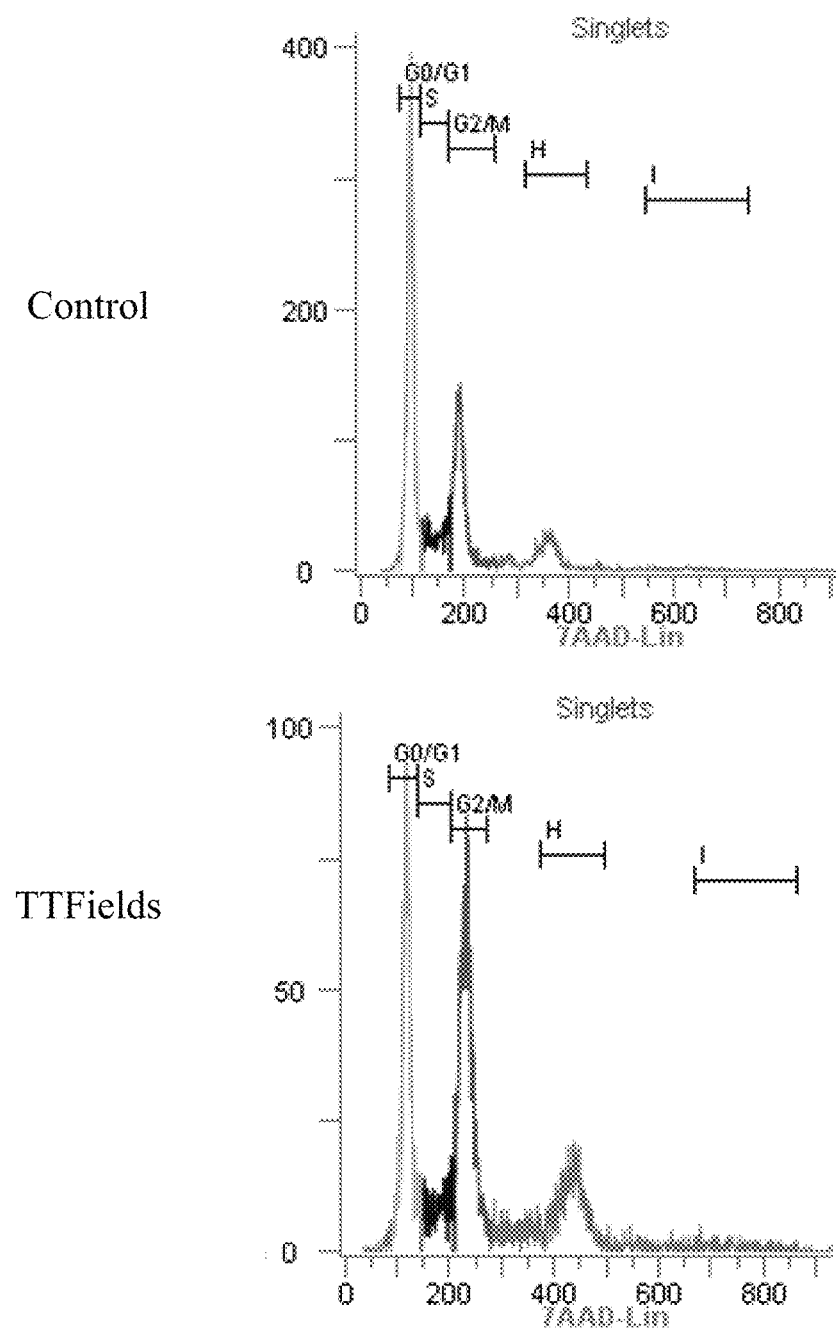
Figure 3D:
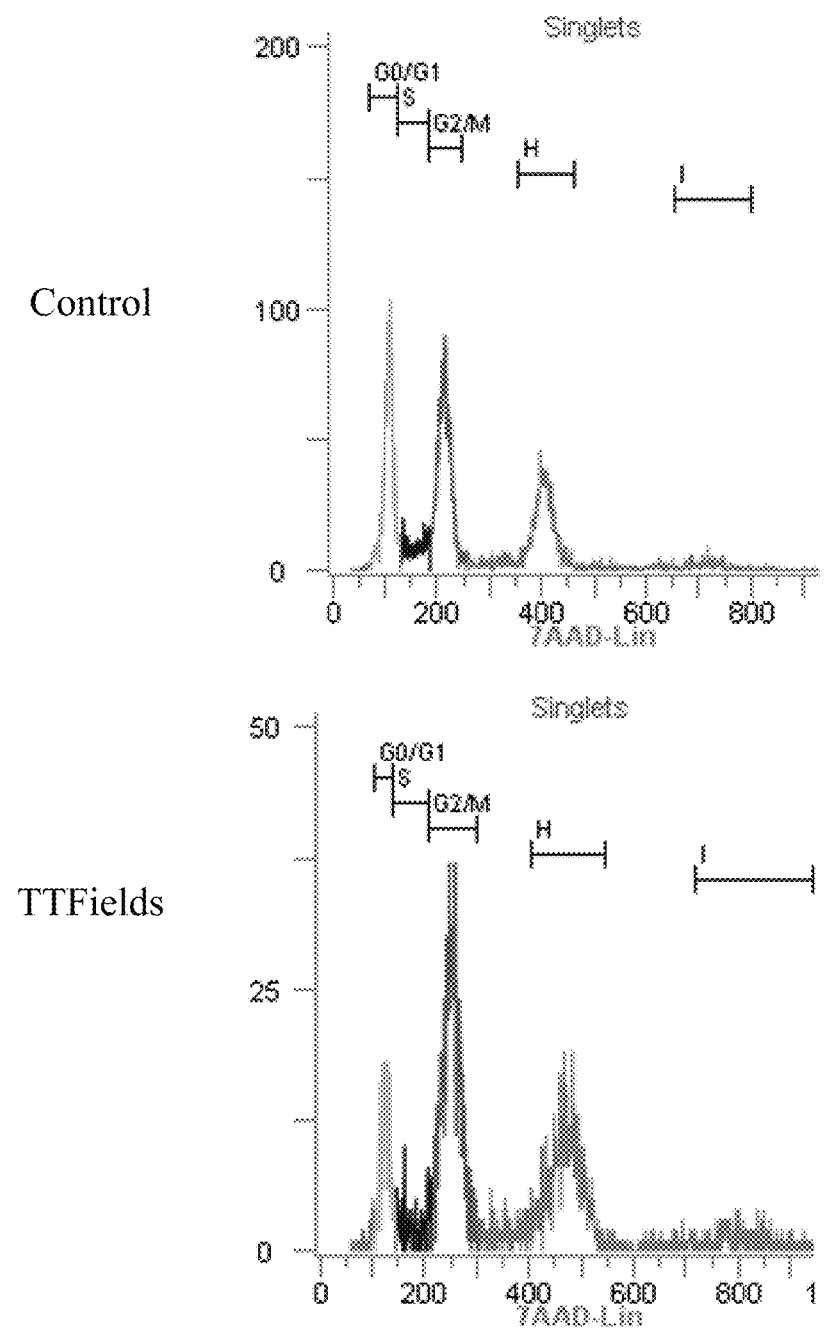
Figure 4A:
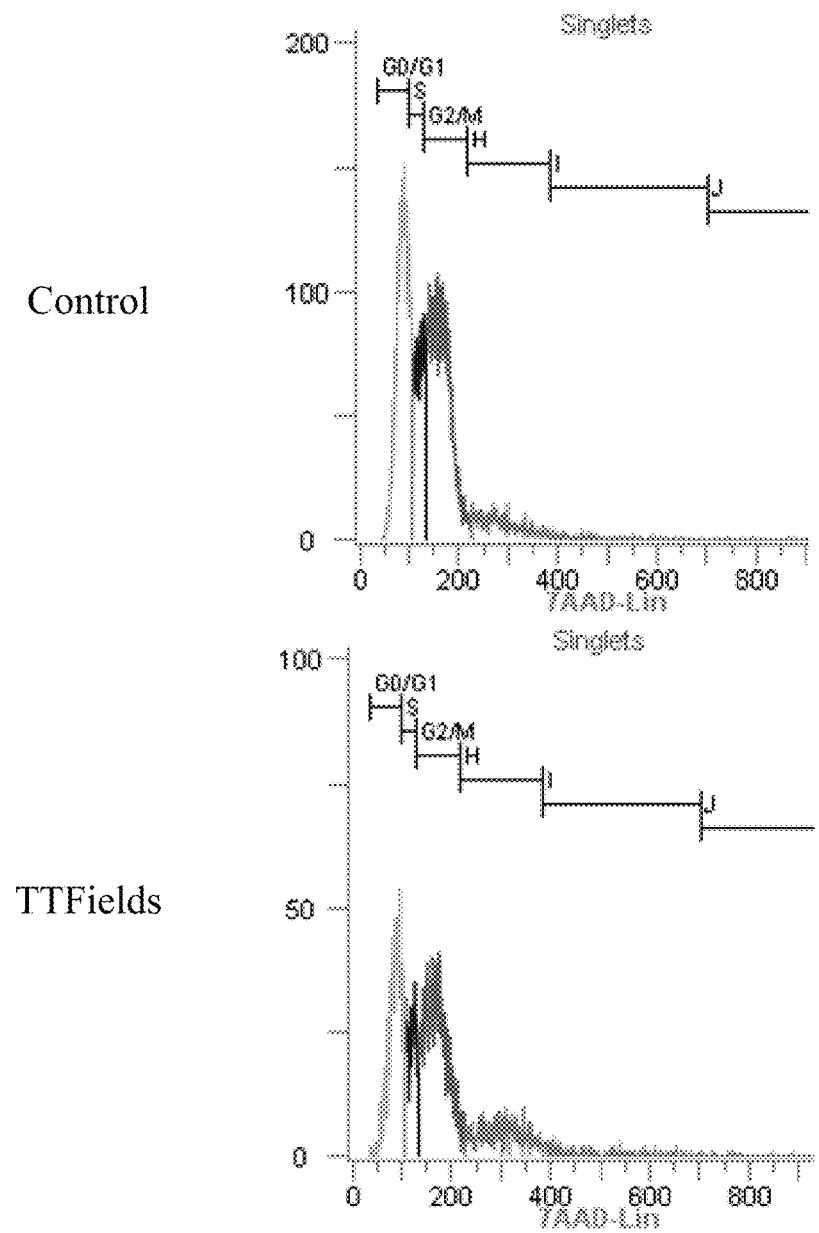
FIGS. 4A-4E show the exemplary increase in polyploidy in U87-MG$^{shP53}$ cells following treatment with TTFields at various AZD1152 concentrations.
Figure 4B:
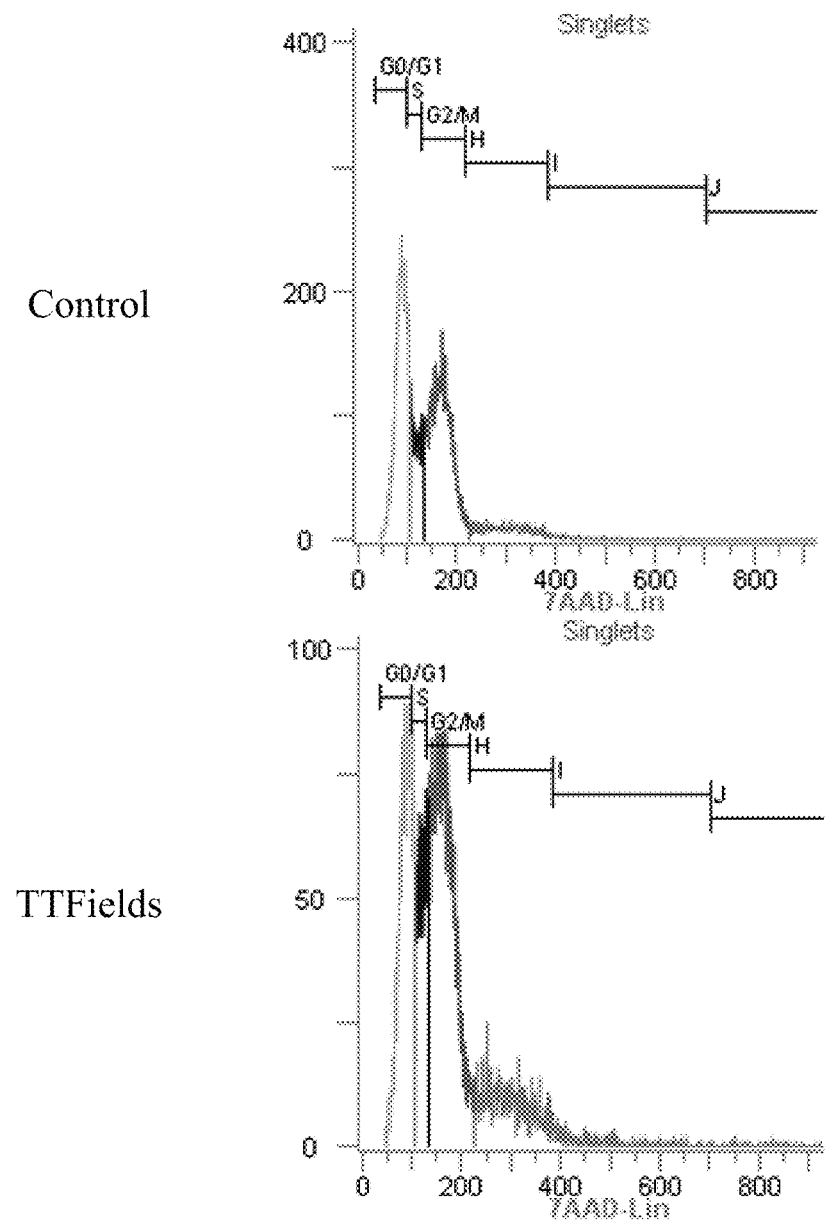
Figure 4C:
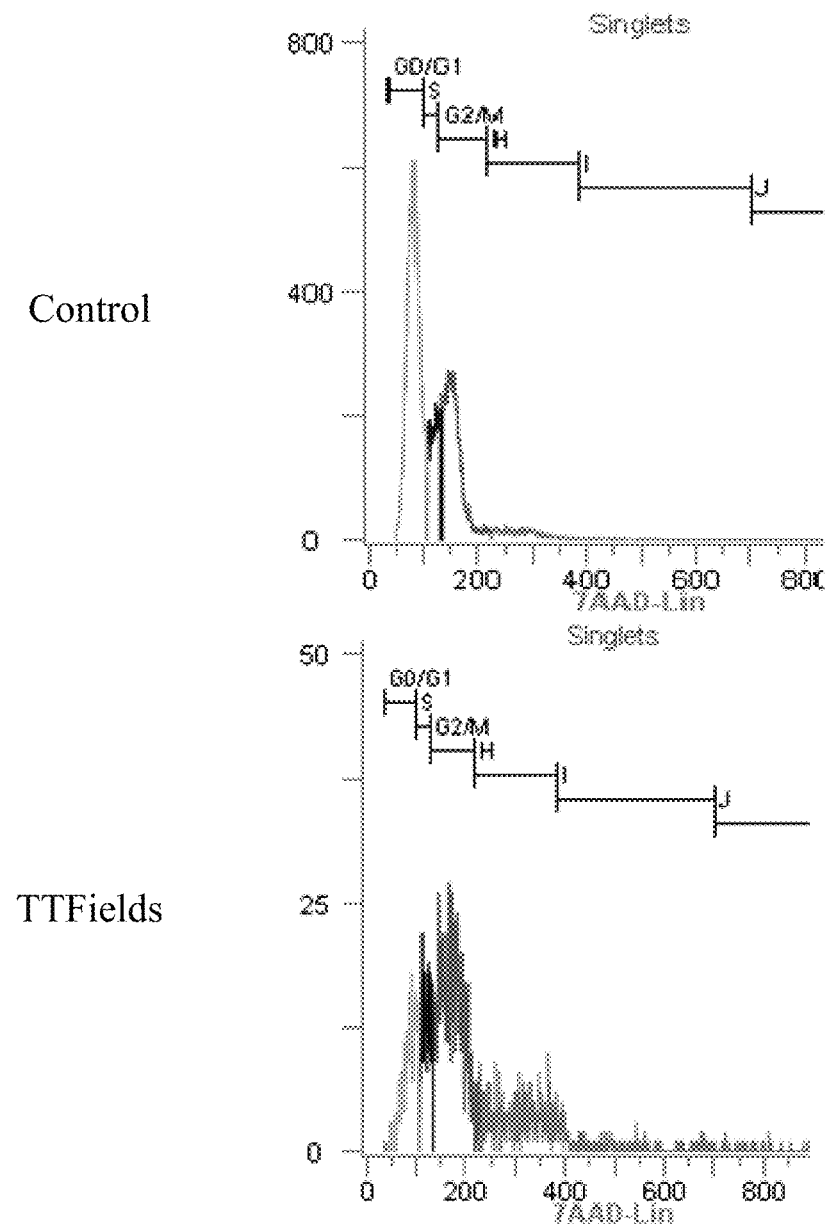
Figure 4D:
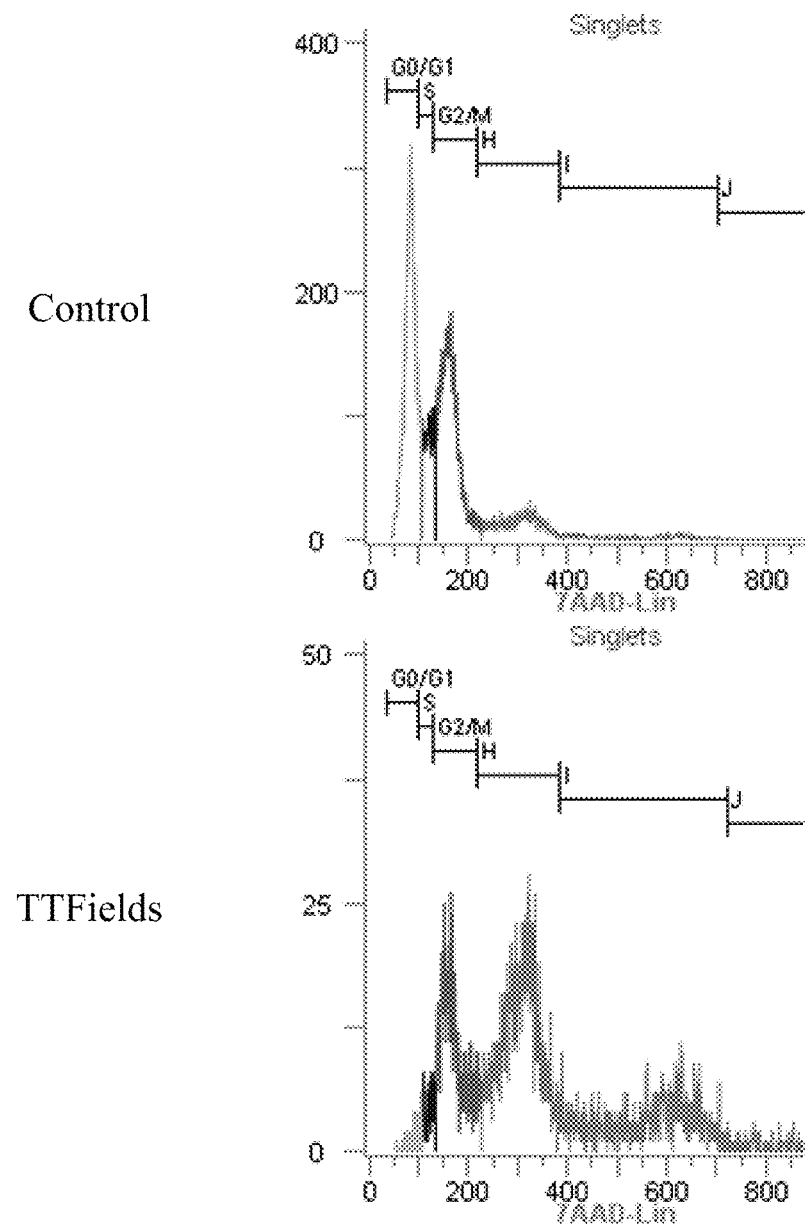
Figure 4E:
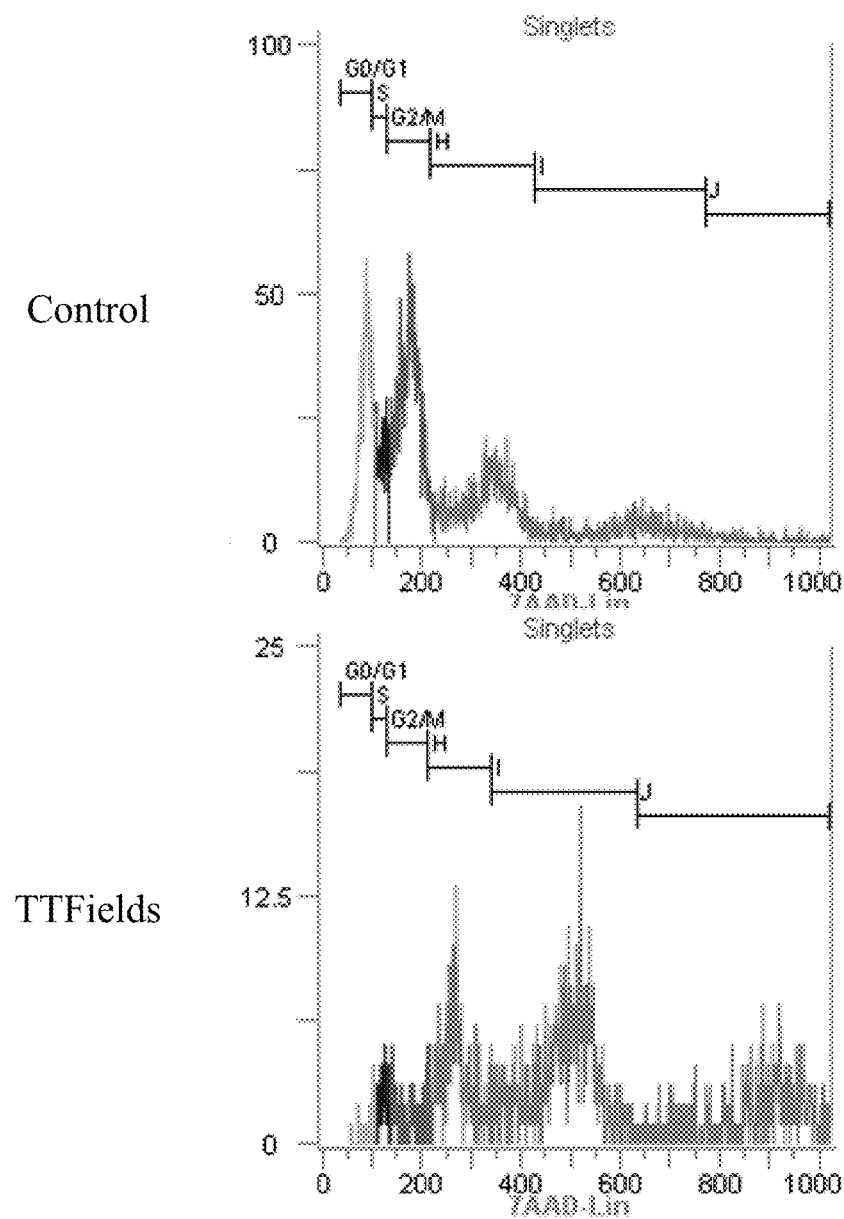

FIGS. 2A and 2B depict the formation of multinuclear cells following the combined treatment of TTFields and AZD1152. FIGS. 2A and 2B are microscopy images of U87-MG and U87-MG$^{shp53}$ cells, respectively, that show the formation of multinuclear and pyknotic cells following the combined treatment of TTFields and AZD1152. U87-MG and U87-MG$^{shp53}$ glioma cells grown in various AZD1152 concentrations were treated with TTFields (200 kHz, 1.6 V/cm RMS) for 72 hours. Cells stained with crystal violet after treatment were imaged under an inverted microscope. The arrows labeled "M" mark multinuclear cells, and the arrows labeled "P" mark pyknotic cells. These images revealed a slight increase in the number of U87-MG multinuclear cells following TTFields application (FIG. 2A, first row). High prevalence of multi nuclear cells (marked by arrows labeled "M") was observed in U87-MG and U87-MG$^{shp53}$ cells exposed to TTFields and a low concentration of AZD1152 (25 nM) as compared to cells treated with AZD1152 (25 nM) alone (FIGS. 2A, 2B middle rows). Cells treated with TTFields and higher doses of AZD1152 (50-100 nM) demonstrated increased rates of pyknosis (marked by arrows labeled "P") (FIGS. 2A, 2B bottom rows).

FIGS. 3A-D and 4A-E show U87-MG and U87-MG$^{shp53}$ FACS analysis of DNA contents following treatment with TTFields and AZD1152. More specifically, FIGS. 3A-D depict increased polyploidy in U87-MG cells following the combined treatment of TTFields (200 kHz, 1.6 V/cm RMS) at various AZD1152 concentrations; and FIGS. 4A-E depict increased polyploidy in U87-MG$^{shp53}$ cells following the combined treatment of TTFields (200 kHz, 1.6 V/cm RMS) at various AZD1152 concentrations. In accordance with multinuclearity observed in the microscopy images, ploidy analysis of U87-MG and U87-mG$^{shp53}$ cells using flow cytometry revealed an increase in the number of polyploid cells following treatment with TTFields and AZD1152.

Tables 1 and 2 depict, for U87-MG and U87-MG$^{shp53}$ respectively, numeric data corresponding to FIGS. 3 and 4. The columns in tables 1 and 2 represent the DNA copy number (e.g., 2n is the normal number of chromosomes (23 pairs=46), 4n is twice the number of chromosomes, etc.).

TABLE 1

| AZD1152 | U87-MG CONTROL | | | | TTFIELDS | | | |
|---|---|---|---|---|---|---|---|---|
| (nM) | 2n | 4n | 8n | 16n | 2n | 4n | 8n | 16n |
| 0 | 62% | 19% | 3% | 0% | 53% | 25% | 3% | 0% |
| 25 | 55% | 25% | 4% | 1% | 39% | 31% | 9% | 2% |
| 50 | 45% | 26% | 8% | 2% | 28% | 36% | 16% | 2% |
| 100 | 27% | 33% | 22% | 3% | 11% | 40% | 25% | 4% |

TABLE 2

| AZD1152 | U87-MGShp53 CONTROL | | | | | TTFIELDS | | |
|---|---|---|---|---|---|---|---|---|
| (nM) | 2n | 4n | 8n | 16n | 32n | 2n | 4n | 8n |
| 0 | 53% | 27% | 4% | 1% | 0% | 50% | 32% | 13% |
| 12.5 | 46% | 29% | 6% | 1% | 0% | 44% | 34% | 19% |
| 25 | 48% | 25% | 6% | 1% | 0% | 10% | 36% | 29% |
| 50 | 40% | 33% | 11% | 3% | 0% | 2% | 21% | 38% |

Tables 3 and 4 depict cytotoxicity and overall effect, respectively, for U87-MG and U87-MG$^{shp53}$, and U-251 cells when exposed to AZD1152 at different concentrations, both alone and combined with TTFields. Because the observed percentage values are lower than the expected percentage values for all nonzero concentrations of AZD1152, this data indicates that synergy is present between TTFields and AZD1152.

TABLE 3

| AZD1152 (nM) | AZD1152 | Observed TTFields + AZD1152 | Expected |
|---|---|---|---|
| U87-MG$^{shp53}$ cytotoxic effect | | | |
| 0 | 100 | 59.5 | 59.5 |
| 25 | 71 | 22.5 | 42.2 |
| 50 | 46.5 | 10.5 | 27.7 |
| 100 | 15 | 4.5 | 8.9 |
| U87-MG cytotoxic effect | | | |
| 0 | 100 | 51.0 | 51.0 |
| 25 | 46 | 13.5 | 23.5 |
| 50 | 25.5 | 8.5 | 13.0 |
| 100 | 9.5 | 4.0 | 4.8 |

TABLE 4

| AZD1152 (nM) | AZD1152 | Observed TTFields + AZD1152 | Expected |
|---|---|---|---|
| U87-MG$^{shp53}$ overall effect | | | |
| 0 | 100 | 64.5 | 64.5 |
| 25 | 79 | 39.0 | 51.0 |
| 50 | 52.5 | 13.0 | 33.9 |
| 100 | 11 | 2.5 | 7.1 |
| U87-MG overall effect | | | |
| 0 | 100 | 48.5 | 48.5 |
| 25 | 31 | 10.0 | 15.0 |
| 50 | 16.5 | 6.0 | 8.0 |
| 100 | 4.5 | 4.0 | 2.2 |
| U-251 overall effect | | | |
| 0 | 100 | 55.0 | 55.0 |
| 6.25 | 74 | 8.0 | 40.7 |
| 12.5 | 15 | 0.7 | 8.3 |
| 25 | 2 | 0.2 | 1.1 |
| 50 | 2 | 0.2 | 1.1 |
| 100 | 1.5 | 0.2 | 0.8 |

Additional Methods

In addition to U87-MG cells, primary tumor-cell lines were established from glioblastoma tissue taken intraoperatively. TTFields (1.6 V/cm RMS, 200 kHz) were applied for 72 hours using the Inovitro™ system. AZD1152 was added to the media in concentrations of up to 100 nmol/l. Cell counts, cell cycle and clonogenic potential were determined at the end of treatment.

Primary tumor-cell-lines were analyzed. In addition, MLN8237, an Aurora A kinase inhibitor, was tested in concentrations up to 50 nmol/l for the treatment of U87-MG and primary tumor-cell lines to further establish Aurora kinase inhibition as a target for combination therapy with TTFields.

Additional Results

Figure 5A:
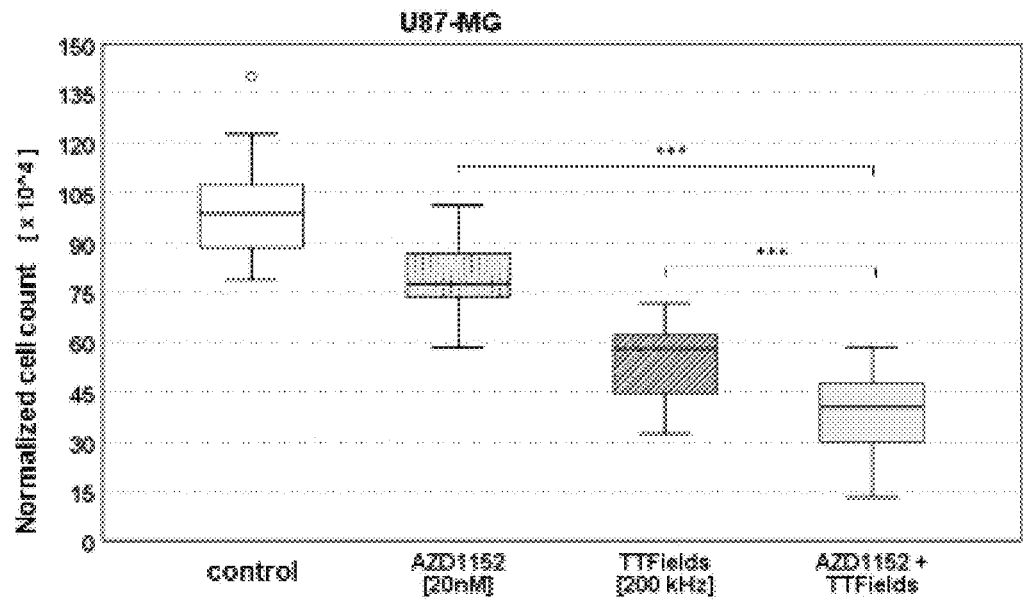
FIGS. 5A and 5B show the normalized cell counts after treatment with TTFields and AZD1152, alone and in combination, on U87-MG (FIG. 5A) and primary glioblastoma cell line HT12347 (FIG. 5B) at the indicated AZD1152 concentration and TTField frequency.
Figure 5B:
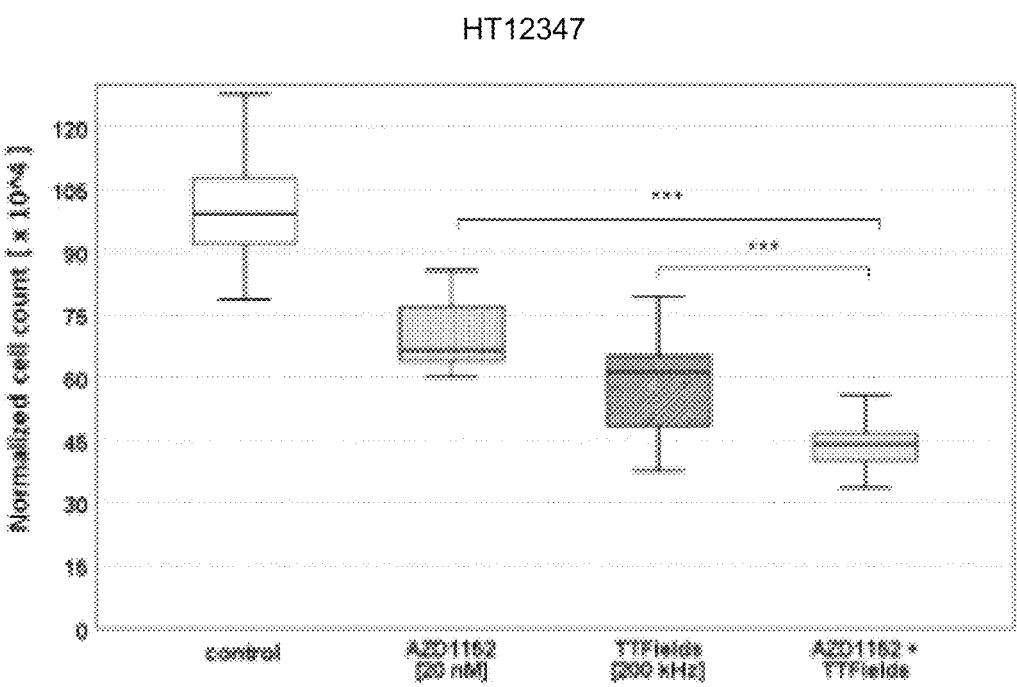

The combined treatment of TTFields and AZD1152 led to a significant reduction in the number of primary glioblastoma cells (Mann-Whitney-U-test, p<0.001) as compared to each treatment alone. FIGS. 5A and 5B show the normalized cell counts after treatment with TTFields and AZD1152, alone and in combination, on U87-MG (FIG. 5A) and primary glioblastoma cell line HT12347 (FIG. 5B) at the indicated AZD1152 concentration and TTField frequency. The exemplary box plots show the normalized cell count after treatment with AZD1152 alone, TTFields alone, and combination of AZD1152 and TTFields. "***" marks significant differences where p<0.001.

Figure 6:
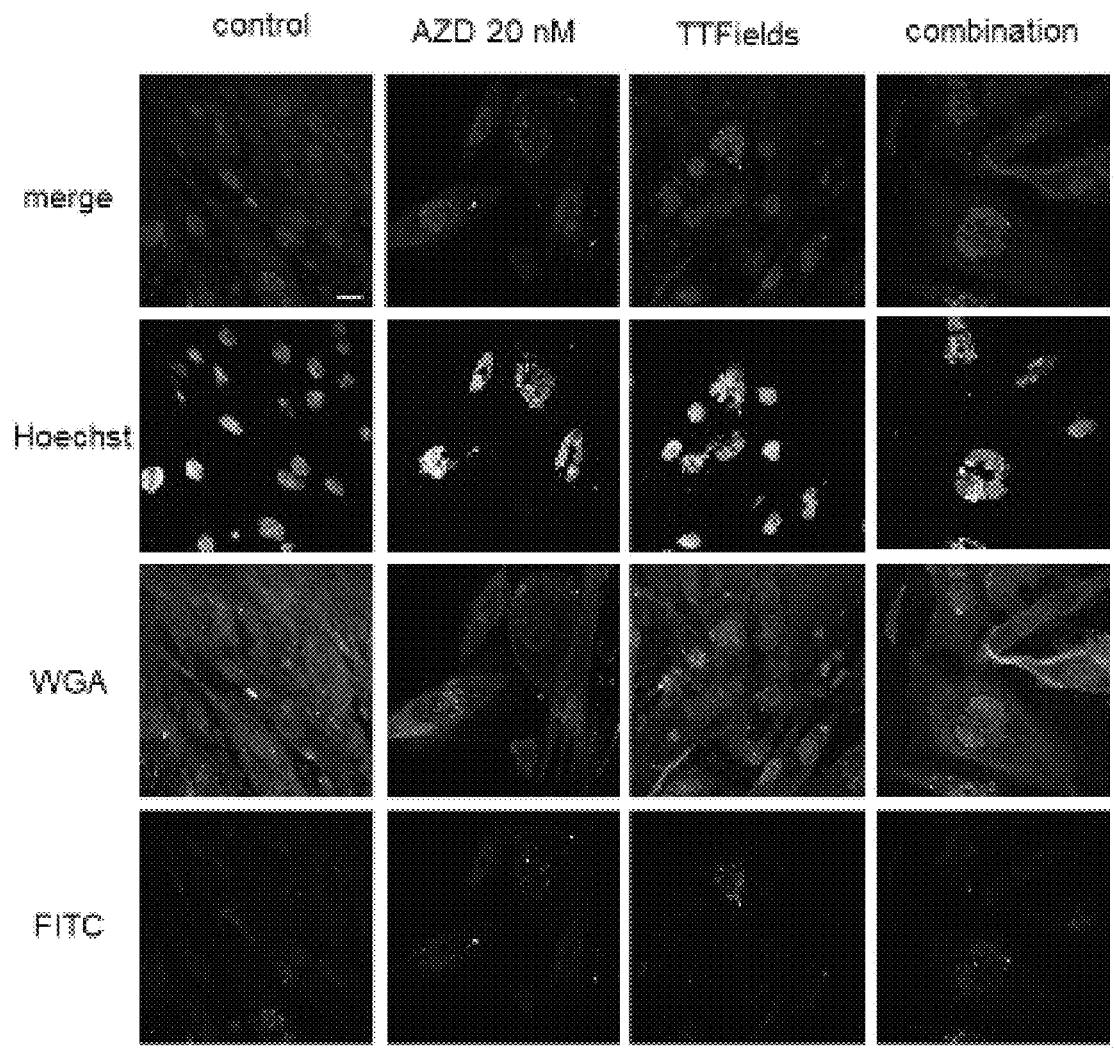
FIG. 6 shows exemplary laser-scanning-microscopy images of primary glioblastoma cell line HT12347 treated and stained as indicated.

FIG. 6 shows exemplary laser-scanning-microscopy images of primary glioblastoma cell line HT12347 treated and stained as indicated. Confocal laser-scanning-microscopy of primary glioblastoma cell-line HT18584 are shown as follows: (1) DNA staining with Hoechst33342(blue), (2) WGA-Alexa Fluor 647 staining for cell membranes (red), and (3) secondary antibody anti-sheep-a-mouse IgG1 FITC for yH2AX staining. The bar marks 25 µm. Cells were treated with control, AZD1152 (20 nM), TTFields, or a combination of both. The greatest reduction in cell number can be seen with the combination treatment.

Figure 7:
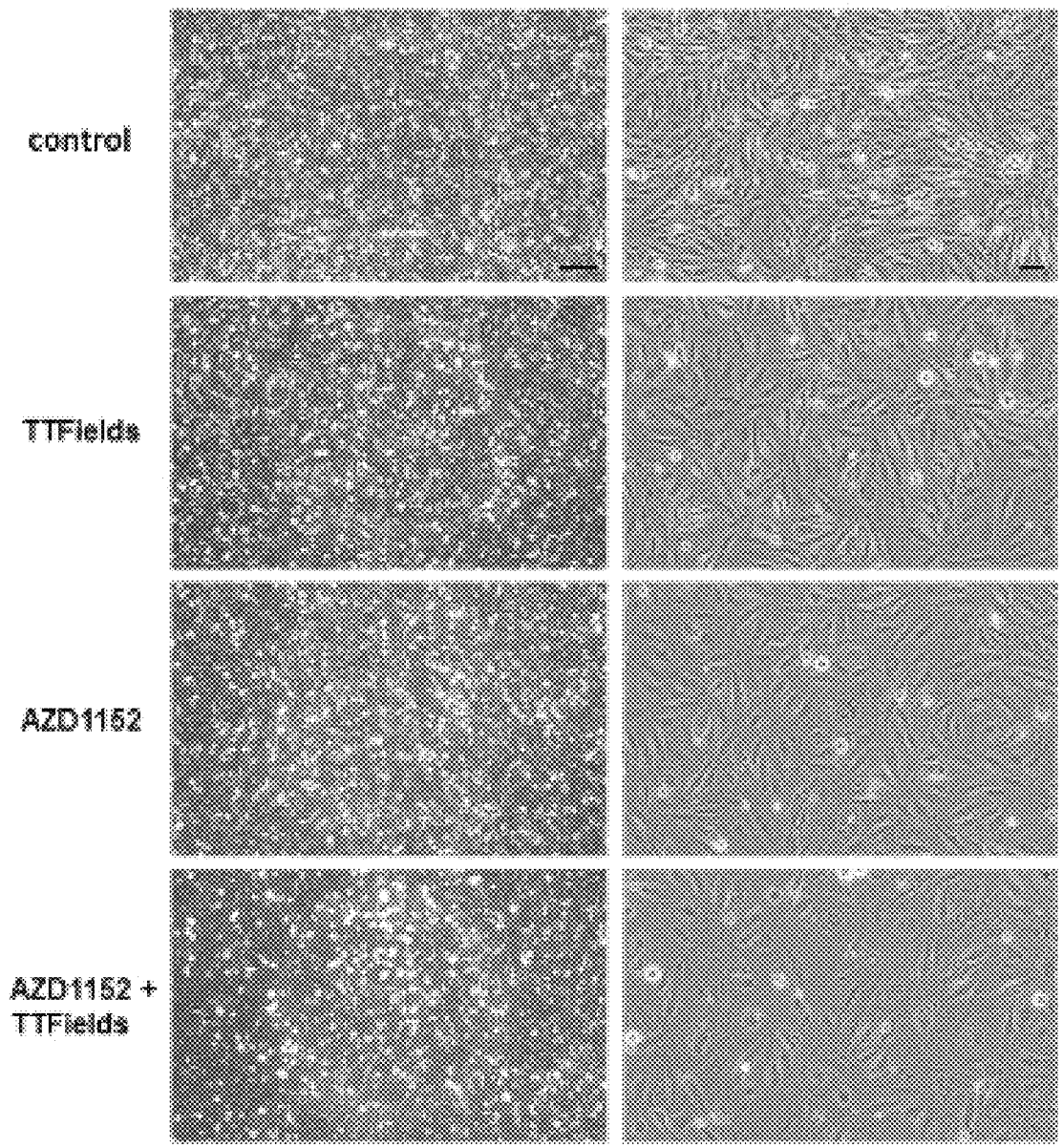
FIG. 7 shows exemplary light-microscopy of primary glioblastoma cell line HT12347 treated as indicated at 2.5× magnification (left) and 10× magnification (right) with the bar on the left marking 200 µM and the bar on the right marking 100 µM.

FIG. 7 shows exemplary light-microscopy of primary glioblastoma cell line HT12347 at 2.5× magnification (left) and 10× magnification (right) with the bar on the left marking 200 µM and the bar on the right marking 100 µM. Cells were treated with control, AZD1152, TTFields, or a combination of both. The greatest reduction in cell number can be seen with the combination treatment.

Figure 8A:
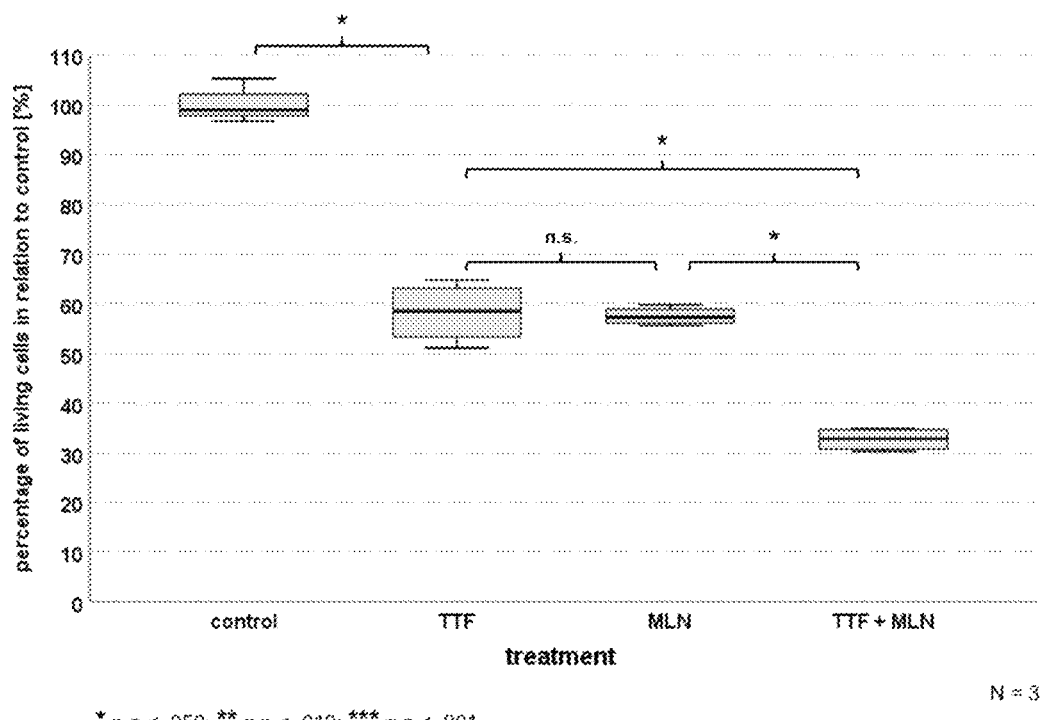
FIGS. 8A and 8B show the normalized cell counts after treatment with TTFields and MLN8337, alone and in combination, on U87-MG (FIG. 8A) and primary glioblastoma cell line HT12347 (FIG. 8B).
Figure 8B:
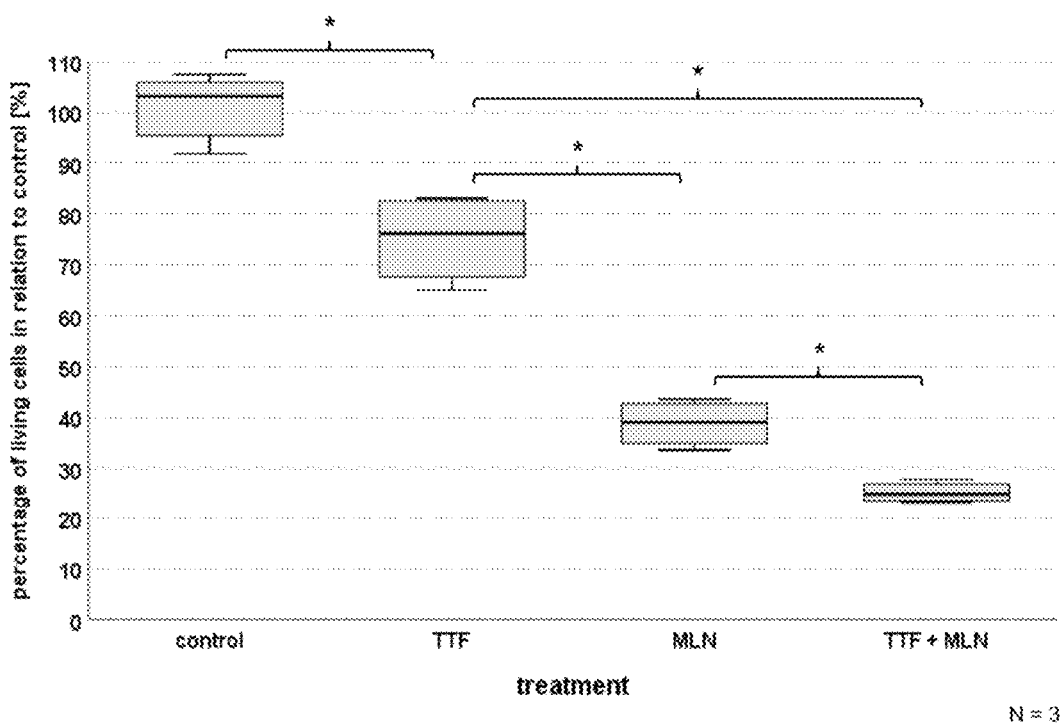

The combined treatment of MLN8237 and TTFields also resulted in a significant decrease of cell numbers as well of U87-MG as primary glioblastoma cell-lines compared to each treatment alone (Mann-Whitney-U-test, p<0.01). FIGS. 8A-8B show the normalized cell counts after treatment with TTFields and MLN8237, alone and in combination, on U87-MG (FIG. 8A) and primary glioblastoma cell line HT12347 (FIG. 8B). The exemplary box plots show the normalized cell count after treatment with TTFields alone, MLN8237 alone, and combination of MLN8237 and TTFields in U87 cells (FIG. 4A), and in HT12347 glioblastoma cells (FIG. 8B). The greatest reduction in the percentage of living cells in relation to the control is shown with the combination of TTFields and MLN8237.

Figure 9A:
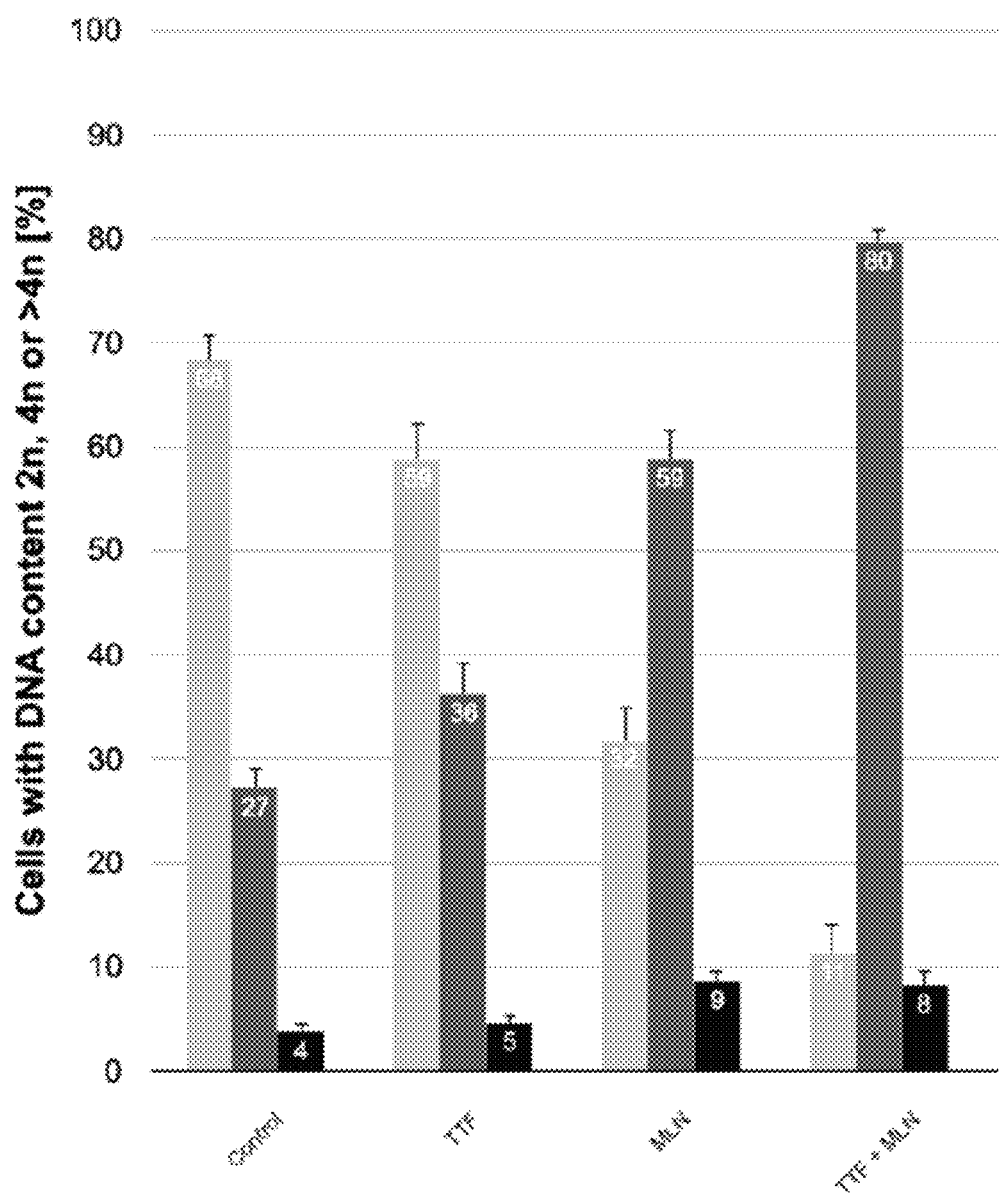
FIG. 9A is a summary of exemplary PI (propium iodide) staining results showing DNA content after treatment with control, TTFields alone, MLN8337 alone, and in combination in glioblastoma cell line HT 12347.
Figure 9B:
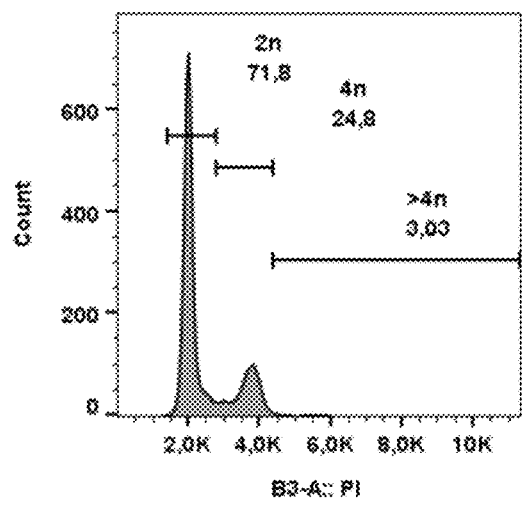
FIGS. 9B-9E are cell cycle histograms that correspond to FIG. 9A.
Figure 9C:
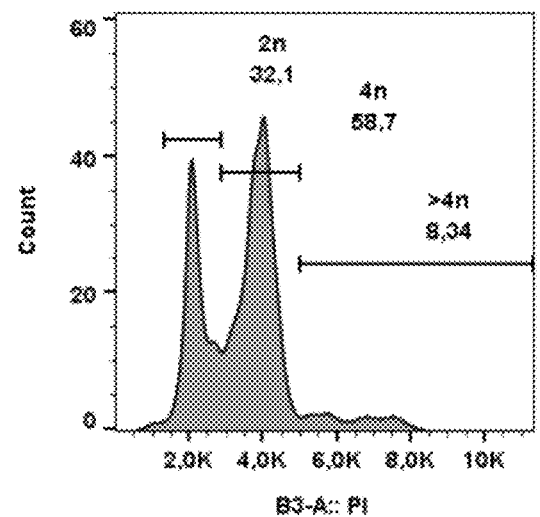
Figure 9D:
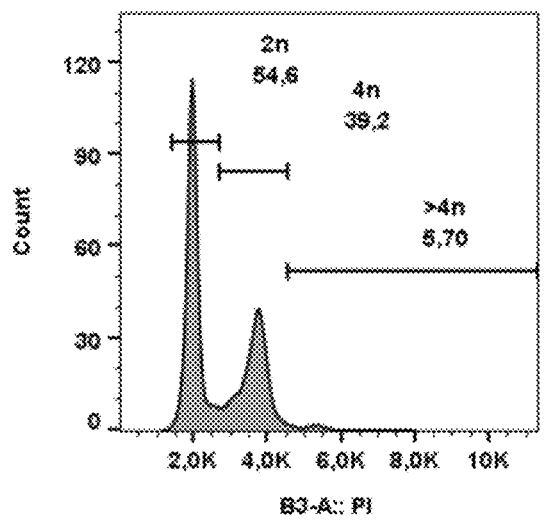
Figure 9E:
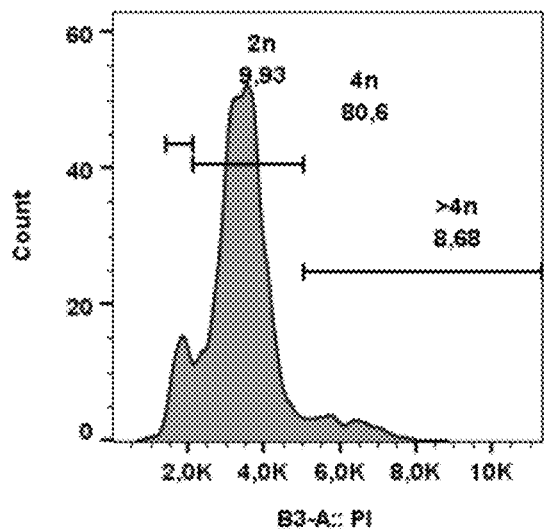
Figure 10A:
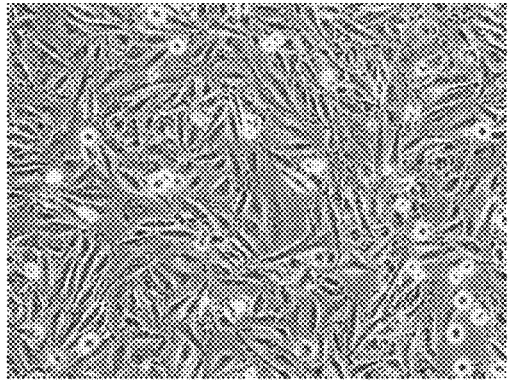
FIGS. 10A-10D show exemplary light microscopy images of primary glioblastoma cells HT12347 after the following treatment: 10A: control; 10B: after TTField treatment; 10C: after treatment with MLN8237 alone; and 10D: after treatment with TTFields and MLN8237.
Figure 10B:
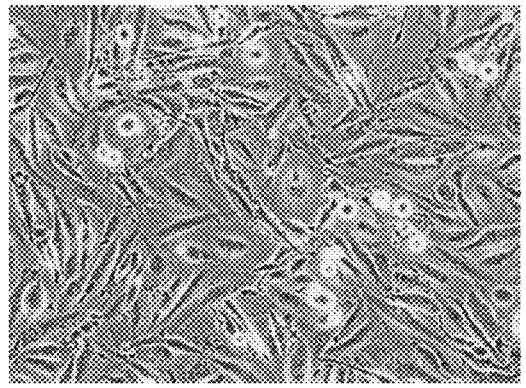
Figure 10C:
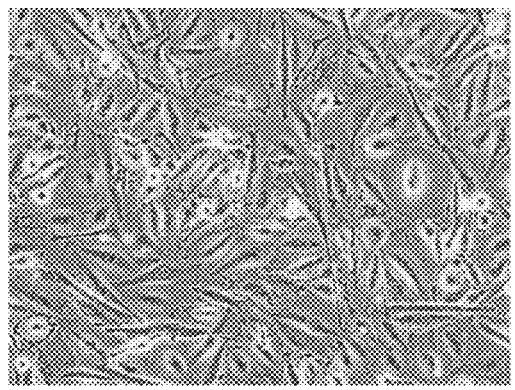
Figure 10D:
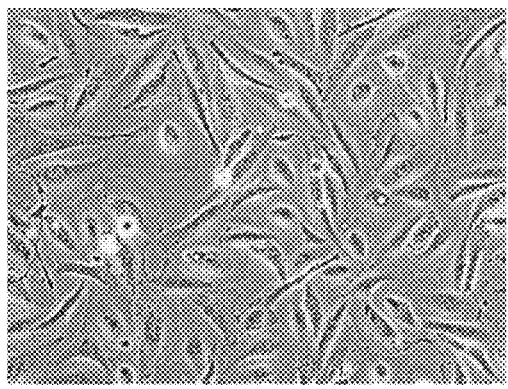

FIGS. 9A-9E show exemplary PI (propium iodide) staining results showing DNA content after treatment with TTFields alone, MLN8337 alone, and in combination in glioblastoma cell line HT 12347 with corresponding cell cycle histograms. FIG. 9A is a summary, with 2n in light gray, 4n in dark gray, and r>4n in black; FIG. 9B is a cell cycle histogram for the control; FIG. 9C is a cell cycle histogram for TTField treatment alone; FIG. 9D is a cell cycle histogram for MLN8237 alone; and FIG. 9E is a cell cycle histogram for TTFields combined with MLN8237. The combination treatment resulted in a higher number of multinuclear and polyploid cells.

FIGS. 10A-10D show exemplary light microscopy images of primary glioblastoma cells HT12347 after the following treatment: 10A: control; 10B: after TTField treatment; 10C: after treatment with MLN8237 alone; 10D: after treatment with TTFields and MLN8237. The combination treatment showed the lowest number of cells.

The results demonstrate that the combination of TTFields and an Aurora kinase inhibitor (e.g., an Aurora A kinase inhibitor or an Aurora B kinase inhibitor) can be an effective treatment against cancer cells, including glioblastoma cells.

CONCLUSIONS

The studies described herein demonstrate that TTFields effect on tumor cells can be exaggerated by an additional inhibition of cytokinesis through chemical inhibition of Aurora kinase (e.g., Aurora A kinase and Aurora B kinase). More specifically, the studies explored combining TTFields and the Aurora B kinase inhibitor AZD1152 or the Aurora A kinase inhibitor MLN8237 for the treatment of GBM. In another instance, additional Aurora kinase inhibitors can be used before, during, or after treatment with TTFields including, but not limited to Danusertib (PHA-739358), AT9283, PF-03814735, and AMG 900.

In U87-MG and U87-MG$^{shp53}$ cells, the combination of TTFields and AZD1125 led to a significant reduction in cell number as compared to each treatment alone. In all 3 tested cell lines, the overall effect of the combined treatment was significantly higher than the effect of each treatment alone. The combination of TTFields and lower doses of AZD1125 led to an increase in the number of multinuclear and polyploid cells, similar to the observed effect of higher AZD1152 concentrations.

These results establish that the viability of cancer cells can be reduced by administering an Aurora B kinase inhibitor to the cancer cells and applying an alternating electric field with a frequency between 100 and 300 kHz to the cancer cells. In some instances of the methods described herein, at least a portion of the applying step is performed simultaneously with at least a portion of the administering step.

In the cells tested as described herein, the combination of TTFields and AZD1125 or MLN8237 led to a significant reduction in cell number as compared to each treatment alone. In all tested cell lines, the overall effect of the combined treatment was significantly higher than the effect of each treatment alone. The combination of TTFields and MLN8337 led to an increase in the number of multinuclear and polyploid cells.

These results establish that the viability of cancer cells can be reduced by administering an Aurora kinase inhibitor (e.g., an Aurora A kinase Inhibitor, an Aurora B kinase inhibitor) to the cancer cells and applying an alternating electric field with a frequency between 100 and 300 kHz to the cancer cells. In some instances of the methods described herein, at least a portion of the applying step is performed simultaneously with at least a portion of the administering step.

Note that while the studies described herein were performed using the frequencies, field intensities, and durations noted above, those parameters may be varied. For example, the frequency could be 200 kHz, between 180 and 220 kHz, or between 100 and 300 kHz; the electric field intensity could be between 0.5 and 5 V/cm, or at least 1 V/cm; and the duration could be anything longer than 8 hours.

Note also that while the studies described herein were all performed in vitro, the results of those studies can be extended to the in vivo context by performing the administering and the applying to living subjects (e.g. using the Optune® system) instead of to cancer cells in vitro.

Note that in the in vitro context, the administering of the Aurora B kinase inhibitor or Aurora A kinase inhibitor to the cancer cells occurs continuously from a first time ($t_1$) when the Aurora B kinase inhibitor or Aurora A kinase inhibitor is introduced into the container that is holding the cancer cells until such time ($t_2$) as the Aurora B kinase inhibitor or Aurora A kinase inhibitor is removed or exhausted. As a result, if TTFields are applied to the cancer cells between $t_1$ and $t_2$, the applying will be simultaneous with at least a portion of the administering. In the in vivo context, the administering of the Aurora B kinase inhibitor or Aurora A kinase inhibitor to the cancer cells occurs continuously from a first time ($t_1$) when the Aurora B kinase inhibitor or Aurora A kinase inhibitor is circulating in the patient's body (e.g., after administering it systemically) or introduced into the vicinity of the cancer cells until such time ($t_2$) as the Aurora B kinase inhibitor or Aurora A kinase inhibitor is eliminated from the patient's body or exhausted. As a result, if TTFields are applied to the cancer cells between $t_1$ and $t_2$, the applying will be simultaneous with at least a portion of the administering.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of reducing viability of cancer cells, the method comprising:
   administering an Aurora kinase inhibitor to the cancer cells; and
   applying an alternating electric field to the cancer cells, the alternating electric field having a frequency between 100 and 300 kHz.

2. The method of claim 1, wherein the Aurora kinase inhibitor comprises an Aurora A kinase inhibitor.

3. The method of claim 1, wherein the Aurora kinase inhibitor comprises an Aurora B kinase inhibitor.

4. The method of claim 1, wherein the Aurora kinase inhibitor comprises MLN8237.

5. The method of claim 1, wherein the Aurora kinase inhibitor comprises AZD1152.

6. The method of claim 1, wherein the Aurora kinase inhibitor comprises an Aurora kinase inhibitor selected from the group consisting of AZD1152, Alisertib (MLN8237), Danusertib (PHA-739358), AT9283, PF-03814735, and AMG 900.

7. The method of claim 1, wherein at least a portion of the applying step is performed simultaneously with at least a portion of the administering step.

8. The method of claim 1, wherein the applying step has a duration of at least 72 hours.

9. The method of claim 1, wherein the frequency of the alternating electric field is between 180 and 220 kHz.

10. The method of claim 1, wherein the Aurora kinase inhibitor is administered to the cancer cells at a therapeutically effective concentration, and wherein the alternating electric field has a field strength of at least 1 V/cm in at least some of the cancer cells.

11. The method of claim 10, wherein the therapeutically effective concentration of the Aurora kinase inhibitor is reduced by at least 50% with respect to a dosage of the Aurora kinase inhibitor known to be therapeutically effective in the absence of an alternating electric field.

12. The method of claim 10, wherein the therapeutically effective concentration of the Aurora kinase inhibitor is from about 12.5 nM to about 100 nM.

13. The method of claim 10, wherein the therapeutically effective concentration of the Aurora kinase inhibitor is from 25 nM to 75 nM.

14. A method of treating cancer in a subject, the method comprising:
    administering a therapeutically effective dose of an Aurora kinase inhibitor to the subject; and
    applying an alternating electric field to a target region of the subject, the alternating electric field having a frequency between 100 and 300 kHz.

15. The method of claim 14, wherein the Aurora kinase inhibitor comprises an Aurora A kinase inhibitor.

16. The method of claim 14, wherein the Aurora kinase inhibitor comprises an Aurora B kinase inhibitor.

17. The method of claim 14, wherein the Aurora kinase inhibitor comprises AZD1152.

18. The method of claim 14, wherein the Aurora kinase inhibitor comprises MLN8237.

19. The method of claim 14, wherein the cancer comprises Glioblastoma.

20. The method of claim 14, wherein the Aurora kinase inhibitor comprises an Aurora kinase inhibitor selected from the group consisting of AZD1152, Alisertib (MLN8237), Danusertib (PHA-739358), AT9283, PF-03814735, and AMG 900.

21. The method of claim 14, wherein at least a portion of the applying step is performed after the administering step and before the Aurora kinase inhibitor is eliminated from the subject's body or exhausted.

22. The method of claim 14, wherein the applying step has a duration of at least 72 hours.

23. The method of claim 14, wherein the frequency of the alternating electric field is between 180 and 220 kHz.

24. The method of claim 14, wherein the alternating electric field has a field strength of at least 1 V/cm in at least a portion of the target region.

25. The method of claim 14, wherein the therapeutically effective dose of the Aurora kinase inhibitor is reduced by at least 50% with respect to a dosage of the Aurora kinase inhibitor known to be therapeutically effective in the absence of an alternating electric field.

26. The method of claim 14, wherein the therapeutically effective dose of the Aurora kinase inhibitor is from about 12.5 nM to about 100 nM.

27. The method of claim 14, wherein the therapeutically effective dose of the Aurora kinase inhibitor is from 25 nM to 75 nM.

* * * * *